US011317794B2

(12) United States Patent
Sorimoto et al.

(10) Patent No.: US 11,317,794 B2
(45) Date of Patent: May 3, 2022

(54) OBSERVATION DEVICE, OBSERVATION UNIT, AND OBSERVATION METHOD

(71) Applicant: J. MORITA MFG. CORP., Kyoto (JP)

(72) Inventors: Keisuke Sorimoto, Kyoto (JP); Tsuyoshi Tanaka, Kyoto (JP); Masayuki Sano, Kyoto (JP); Ryosuke Kaji, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 0 days.

(21) Appl. No.: 16/762,678

(22) PCT Filed: Nov. 8, 2018

(86) PCT No.: PCT/JP2018/041516
§ 371 (c)(1),
(2) Date: May 8, 2020

(87) PCT Pub. No.: WO2019/093426
PCT Pub. Date: May 16, 2019

(65) Prior Publication Data
US 2021/0169318 A1 Jun. 10, 2021

(30) Foreign Application Priority Data

Nov. 9, 2017 (JP) .............................. JP2017-216338

(51) Int. Cl.
*A61B 1/00* (2006.01)
*A61B 1/045* (2006.01)
(Continued)

(52) U.S. Cl.
CPC ............ *A61B 1/24* (2013.01); *A61B 1/00009* (2013.01); *A61B 1/00048* (2013.01);
(Continued)

(58) Field of Classification Search
None
See application file for complete search history.

(56) References Cited

U.S. PATENT DOCUMENTS

| 2010/0215220 A1 | 8/2010 | Yamaguchi et al. | |
| 2014/0099604 A1* | 4/2014 | Kurpis | A61C 19/05 433/223 |
| 2015/0310668 A1* | 10/2015 | Ellerbrock | A61C 1/084 345/633 |

FOREIGN PATENT DOCUMENTS

| JP | H0616099 B2 | 3/1994 |
| JP | H11253433 A | 9/1999 |

(Continued)

OTHER PUBLICATIONS

International Search Report issued in International Application No. PCT/JP2018/041516, dated Feb. 12, 2019 (5 pages).

(Continued)

*Primary Examiner* — Patricia I Young
(74) *Attorney, Agent, or Firm* — Osha Bergman Watanabe & Burton LLP

(57) ABSTRACT

A magnifying glass captures an image of a tooth by a plurality of cameras for observation. The plurality of cameras includes a narrow range camera capturing a narrow range image of the tooth and a wide range camera capturing a wide range image of the tooth. The magnifying glass includes a three-dimensional position calculator detecting a three-dimensional position of at least the tooth based on the wide range image; a blur correction processor correcting a blur of the narrow range image, based on a change in a three-dimensional positional relationship between the tooth, the three-dimensional position of which has been detected by the three-dimensional position detector, and the narrow (Continued)

range camera; and an image display portion displaying at least the narrow range image having the blur corrected.

9 Claims, 14 Drawing Sheets

(51) Int. Cl.
    *A61B 1/06*     (2006.01)
    *A61B 1/24*     (2006.01)
    *A61B 5/107*     (2006.01)
    *H04N 5/232*     (2006.01)
    *A61B 90/50*     (2016.01)

(52) U.S. Cl.
    CPC ............... *A61B 1/045* (2013.01); *A61B 1/06* (2013.01); *H04N 5/232121* (2018.08); *H04N 5/232125* (2018.08); *A61B 5/1077* (2013.01); *A61B 2090/502* (2016.02)

(56) References Cited

FOREIGN PATENT DOCUMENTS

| | | |
|---|---|---|
| JP | 2003052718 A | 2/2003 |
| JP | 2013117848 A | 6/2013 |
| JP | 2017191609 A | 10/2017 |

OTHER PUBLICATIONS

Written Opinion issued in International Application No. PCT/JP2018/041516; dated Feb. 12, 2019 (4 pages).

Office Action issued in Japanese Application No. 2017-216338; dated Jun. 23, 2020 (6 pages).

Extended European Search Report issued in corresponding European Application No. EP18876392.4 dated Jul. 21, 2021 (5 pages).

* cited by examiner

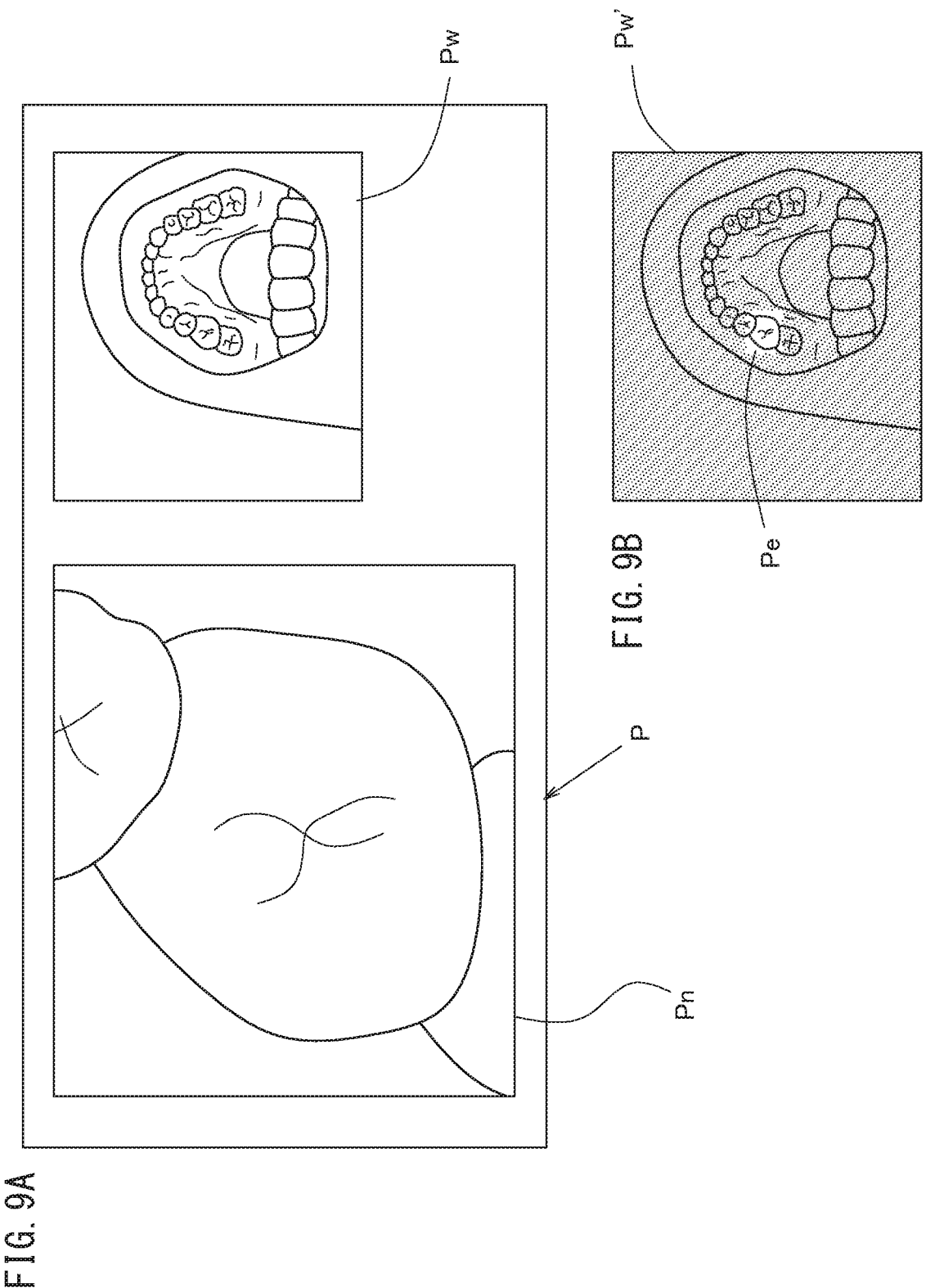

OBSERVATION DEVICE, OBSERVATION UNIT, AND OBSERVATION METHOD

TECHNICAL FIELD

The present invention relates to an observation device, an observation unit, and an observation method by which, for example, a desired observation site in an oral cavity region is observed.

BACKGROUND

Conventionally, for example, in a dental care field or the like, a root canal of a tooth is treated precisely while the tooth is observed with a microscope.

For example, Patent Document 1 describes one of medical care tables with a microscope for such a type of care. The medical care table with a microscope described in Patent Document 1 includes the microscope supported by a support arm located in the vicinity of a medical care table. The operator (observer) may perform a precise medical care while observing an observation site with the microscope. In another example, a magnifying glass (loupe) is attached to the head of the observer, so that the observer performs a precise medical care while observing a magnified observation site.

Such a microscope allows the observation site to be observed precisely at high magnification although the observation site is of a small range. However, a vibration of the support arm that supports the microscope or a tiny movement of an observation subject moves the microscope and the observation site with respect to each other, and such a relative movement is magnified to blur the field of observation. This causes an undesirable possibility that the observation may not be performed precisely. Also in the case of the magnifying glass attachable to the head, especially when the magnification is high, a blur may be caused by the movement of the head of the observer or the movement of the observation subject. The blur may be alleviated by a support arm or a head securing tool formed of a highly rigid material. However, this enlarges the support arm or the head securing tool, or increases the production or installment cost, which may increase the load on the observer.

CITATION LIST

Patent Literature

Patent Document 1: Japanese Laid-Open Patent Publication No. 2003-052718

SUMMARY

In such a situation, one or more embodiments of the present invention may provide an observation device, an observation unit and an observation method allowing an observation site of a small range to be precisely observed while suppressing the blur.

One or more embodiments of the present invention may be directed to an observation device capturing an image of an image capturing site for observation. The observation device includes an image capturing portion capturing the image of the image capturing site, the image capturing portion including a narrow range image capturing portion capturing an image of the observation site in a narrow range and a wide range image capturing portion capturing an image of the observation site in a wide range; a three-dimensional position detector detecting a three-dimensional position of at least the observation site based on a wide range image captured by the wide range image capturing portion; a blur corrector correcting a blur of a narrow range image captured by the narrow range image capturing portion, based on a change in a three-dimensional positional relationship between the observation site, the three-dimensional position of which has been detected by the three-dimensional position detector, and the narrow range image capturing portion; and an image display portion displaying at least the narrow range image having the blur corrected, among the narrow range image having the blur corrected and the wide range image.

One or more embodiments of the present invention is also directed to an observation method for capturing an image of an observation site, for observation, by an image capturing portion of an observation device. The observation method includes detecting a three-dimensional position of at least the observation site based on a wide range image captured by a wide range image capturing portion included in the image capturing portion; correcting a blur of a narrow range image captured by a narrow range image capturing portion included in the image capturing portion, based on a three-dimensional positional relationship between the observation site, the three-dimensional position of which has been detected, and the narrow range image capturing portion; and displaying at least the narrow range image having the blur corrected, among the narrow range image having the blur corrected and the wide range image.

The narrow range image capturing portion and the wide range image capturing portion may be integral with each other, or may be separate from each other, to form the image capturing portion. Even in the case where the narrow range image capturing portion and the wide range image capturing portion are integral with each other to form the image capturing portion, the narrow range image capturing portion and the wide range image capturing portion may be provided independently from each other in a casing of the integral image capturing portion. Each of the image capturing portions includes an optical route including an image capturing element and a lens. The image capturing portions may share a part of the optical routes.

The image display portion may display two types of images corresponding to parallax of the left and right eyes. In this case, the observer may observe the observation site as an a three-dimensional image, which improves the convenience. In order to capture the two types of images, at least the narrow range image capturing portion, among the narrow range image capturing portion and the wide range image capturing portion, may be provided in the number of two so as to capture images of the observation site at two different angles.

The observation device may be attached to the head of the observer like an HMD (Head-Mounted Display), or may be supported by a support. Alternatively, the observation device may be used as being separated from the support and attached to the head of the observer in some cases, and may be used as being separated from the head and attached to the support in some other cases.

The support may be, for example, a support arm extending from a ceiling, a wall, a floor, a stand, a wagon, a rack, or a medical care table, a spittoon table, a medical robot, any other medical device or the like. It is preferred that the support may be a support arm positionally adjustable manually (e.g., a balance arm including a plurality of joints) so as to be movable to a position suitable to the observation in accordance with the position of the observation site, the physique of the patient or the like.

The support may be a robot arm or the like positionally adjustable automatically. In the case where the image capturing portion includes the narrow range image capturing portion and the wide range image capturing portion separate from each other, the narrow range image capturing portion and the wide range image capturing portion may be supported by the same support or different supports. One of the narrow range image capturing portion and the wide range image capturing portion may be directly secured to the ceiling, the wall or the like with no use of the support.

The observation site may be a tooth, the inside of the tooth, a site in the oral cavity such as the gum or the like, or a part of the body of a human or an animal.

The three-dimensional position detector detects a three-dimensional position of the observation site based on a wide range image captured by the wide range image capturing portion. Specifically, the wide range image capturing portion includes a three-dimensional camera such as a stereo camera or the like, and the captured wide range image is processed. Thus, the three-dimensional position of the observation site may be detected based on a characteristic site of the observation site or a characteristic point such as a ball marker or the like rigidly attached to the observation site.

A three-dimensional positional relationship between the observation site, the three-dimensional position of which has been detected by the three-dimensional position detector, and the narrow range image capturing portion may be a three-dimensional positional relationship based on the three-dimensional position of the observation site detected based on the wide range image and the known three-dimensional position of the narrow range image capturing portion with respect to the wide range image capturing portion, a three-dimensional positional relationship based on the three-dimensional position of the observation site detected based on the wide range image and the three-dimensional position of the narrow range image capturing portion, or a three-dimensional positional relationship based on the three-dimensional position of the narrow range image detected by a different three-dimensional position detection device.

The "blur correction of the narrow range image" may be a blur correction on the narrow range image performed in accordance with a change in the three-dimensional positional relationship. For the blur correction, for example, an image process such as a parallel movement of a pixel value, a rotational movement of a pixel value, enlargement/reduction of a pixel value, or the like may be performed. Alternatively, the entirety of the narrow range image capturing portion or a part of the optical route included in the narrow range image capturing portion may be moved in a such a direction as to eliminate the change in the three-dimensional positional relationship so as not to blur the narrow range image. Still alternatively, such methods may be combined.

The entirety of, or a part of the narrow range image capturing portion may be moved, for example, by any of the following methods: according to one method, an actuator is used to mechanically move an optical element such as an image capturing element (image sensor), or a lens, a prism, a mirror or the like included in the optical route; and according to another method, a variable lens, a variable prism, a spatial light modulator or the like that is variable in the refractive index or the shape by electric control is used to optically move the optical axis of the narrow range image capturing portion.

The expression "at least display the narrow range image having the blur corrected" encompasses displaying only the narrow range image, and displaying the narrow range image and the wide range image side by side or in a switching manner.

According to one or more embodiments of this invention, the observation site of the narrow range may be observed precisely while the blur is suppressed.

This will be described in detail. When the three-dimensional positional relationship between the observation site and the narrow range image capturing portion is changed, the above-described blur is caused to the narrow range image. However, the blur of the narrow range image caused by a change in the three-dimensional positional relationship between the three-dimensional position of at least the observation site, detected based on the wide range image captured by the wide range image capturing portion included in the image capturing portion of the observation device, and the narrow range image capturing portion is corrected. Therefore, a clear narrow range image with no blur may be obtained. Thus, the observation site of the narrow range may be observed precisely.

An image of the observation site may be captured in a wide range by the wide range image capturing portion. Therefore, a wide range including the site that is observed by the narrow range image capturing portion may be observed.

The image display portion displaying the narrow range image having the blur corrected, among the narrow range image having the blur corrected and the wide range image, is provided. Therefore, the observation may be performed precisely and comprehensively while the narrow range image of a narrow view field and the wide range image of a wide view field are checked together.

The wide range image and the narrow range image may be displayed on the image display portion side by side simultaneously or in a switching manner. Therefore, while a site in the narrow range is observed precisely, the current position of attention in the view field of the wide range may be checked simultaneously. This improves the operability. Namely, one same wide range image capturing portion may be used, with no increase in the number of components, to provide a combined effect of acting as an image capturing portion that corrects the blur and also of acting as an image capturing portion for comprehensive observation as described above.

The mechanical vibration that causes the blur is permitted. Therefore, the support, even in the case of supporting the observation site, may have a structure that is low in rigidity, namely, that is compact, lightweight and low-cost.

In one or more embodiments of the present invention, the narrow range image capturing portion and the wide range image capturing portion may share at least a part of optical paths thereof.

The optical paths may include an image capturing element such as an image sensor, an optical path, a lens and the like. A part of such components included in the optical paths may be shared.

In the case where the image capturing element is shared, one image capturing element may be divided into a region of the narrow range image capturing portion and a region of the wide range image capturing portion. In order to allow the image capturing element for the narrow range and the image capturing element for the wide range to capture images of different ranges from the shared optical route, a beam splitter or a lens may be installed in the middle of the optical path between the image capturing element and the observation site to branch the optical path.

The image capturing element in the wide range image capturing portion and the image capturing element in the narrow range image capturing portion may be different in the shutter speed, the image capturing rate, the pixel size, the pixel binning size, the structure of the color filter (for color image capturing, for monochromatic image capturing, for infrared image capturing, for visible light image capturing, for ultraviolet image capturing or the like), or the like. In the case where the image capturing element is divided into regions, the different regions may have different specifications.

According to one or more embodiments of this invention, the image capturing portion may be simplified and made compact.

This will be described in detail. In the case where the narrow range image capturing portion and the wide range image capturing portion are separate from each other, or in the case where the narrow range image capturing portion and the wide range image capturing portion are integral with each other but each include an optical route including an image capturing element, an optical path, a lens and the like, the number of the components is increased and the structure is complicated. The optical route of the narrow range image capturing portion and the optical route of the wide range image capturing portion may be shared at least partially to decrease the number of the components and simplify the structure.

In one or more embodiments of the present invention, the observation device may further include a narrow range image capturing portion controller controlling continuous image capturing performed while a focal point position of the narrow range image capturing portion is moved with respect to the observation site; and a narrow range image generator synthesizing a plurality of narrow range images captured as a result of the continuous image capturing to generate a narrow range image having a great depth of field.

Specifically, a narrow range image having a depth of field expanded as a result of synthesis of images (i.e., narrow range image having a great depth of field) may be generated by, for example, the following procedure. (1) Images of the observation site are continuously captured while the position of the focal point is swept on the observation site in the direction of the optical axis by a method of, for example, mechanically driving a lens included in the narrow range image capturing portion. (2) The amount of contrast is calculated (quantization of whether the image is blurred or focused is performed) for each of pixels. While the position of the focal point is swept by, for example, one reciprocal movement (or half reciprocal movement) of the lens over a predetermined distance, the pixel value at the time when the amount of contrast exhibits the maximum value is used for the narrow range image to be displayed on the image display portion. The amount of contrast may be obtained by a known method of using the Laplacian operator, a differential filter or the like. If the plurality of images, captured by the continuous image capturing in order to generate a narrow range image having an expanded depth of field, are blurred, the amount of contrast may, for example, exhibit the maximum value a plurality of times in the calculation of (2), for example. In this case, the narrow range image displayed on the image display portion may be distorted or may have noise. According to one or more embodiments of the present invention, the calculation is performed based on the narrow range image having the blur corrected. Therefore, the above-described situation of the noise or the like may be resolved, and the operability for the observer is improved.

The procedure of (1) and (2) may be performed at high speed by use of a hardware processor such as an FPGA or the like. This may allow a narrow range image having a great depth of field, a little delay and a high frame rate to be displayed on the image display portion, which improves the degree of satisfaction of the observer.

The above-described "movement of the position of the focal point" may be realized by the following methods. According to a method, the image capturing element in the narrow range image capturing portion is secured, and the effective focal length of an optical system including a lens and the like except for the image capturing element is moved (e.g., by a method of mechanically moving at least one element lens, among a plurality of element lenses included in the optical system, forward and rearward along the optical axis, or a method of electrically controlling a focal point variable lens such as a liquid lens or the like included in the optical system to adjust the focal length of the focal point variable lens). According to another method, while the focal length of the optical system is kept at a predetermined distance, the narrow range image capturing portion is physically moved to move the position of the focal point. According to still another method, while the focal length of the optical system is kept at a predetermined distance, the image capturing element is moved along the optical axis. Alternatively, the above-described methods are combined.

According to one or more embodiments of this invention, the observation may be performed more precisely based on the narrow range image having a great depth of field.

This will be described in detail. The narrow range image capturing portion captures an image of the narrow range of the observation site at high magnification. However, the narrow range image captured by the narrow range image capturing portion has a small depth of field, namely, has a small range that is focused in the depth direction. Therefore, the range that may be observed precisely tends to be narrow.

Nonetheless, the continuous image capturing of the observation site is performed while the position of the focal point of the narrow range image capturing portion is moved, and the plurality of narrow range images captured as a result of the continuous image capturing may be synthesized to generate a narrow range image having a great depth of field. Namely, the narrow range image, of the observation site, captured at high magnification and including a wide region focused in the depth direction is generated. Therefore, the observation may be performed precisely.

The plurality of narrow range images, captured as a result of the continuous image capturing performed while the position of the focal point is moved, have the blur corrected. Therefore, the plurality of narrow range images captured as a result of the continuous image capturing may be synthesized with high precision to generate, at high precision, a narrow range image that is clear and has a great depth of field.

Namely, the wide range image capturing portion may provide a combined effect of acting to correct the blur, being usable to generate a narrow range image having a great depth of field with high precision as described above, and realizing the comprehensive observation.

In one or more embodiments of the present invention, the observation device may further include a light projector projecting light toward at least the observation site, an image of which is to be captured by the narrow range image capturing portion, at the time of performing the continuous image capturing under the control of the narrow range image capturing portion controller.

The light projected by the light projector may be pattern light having a predetermined pattern or light with no pattern.

According to one or more embodiments of this invention, the light is projected toward the observation site that is being observed by use of the narrow range image capturing portion of a narrow view field. Therefore, the observation site observed by use of the narrow range image capturing portion may be clearly depicted in the wide range image captured by the wide range image capturing portion. Namely, the light thus projected may clearly depict a site in the narrow range image. The narrow range image and the wide range image may be displayed on the image display portion side by side or in a switching manner. In this case, the observation site in the entirety is made clear, and thus the operability may be improved.

In the case where the light projected by the light projector is pattern light having a predetermined pattern, the light is projected toward at least the observation site, the image of which is to be captured by the narrow range image capturing portion. Therefore, for example, even if being a homogenous structural body with no decorative pattern, the observation site may be provided with a pattern, so that the amount of contrast may be detected easily in the process of (2). Thus, a narrow range image that is clearer and has a greater depth of field may be generated with high precision.

In one or more embodiments of the present invention, the observation device may further include a three-dimensional shape meter measuring a three-dimensional shape of at least the observation site, an image of which is to be captured by the narrow range image capturing portion, the measurement being performed based on focal point position information on the focal point position that is moving during the continuous image capturing performed under the control of the narrow range image capturing portion controller.

Specifically, in the above-described process (2) of generating the narrow range image having a great depth of field, the amount of contrast exhibiting the maximum value in a certain pixel is equivalent to the moving position of the focal point matching the position of the surface of the observation site.

The focal point position information on the moving position of the focal point may be associated with a control state of the narrow range image capturing portion controller (information on the voltage input to the liquid lens, or information on the current position of the lens mechanically moving, the position being detectable by use of an encoder sensor or the like). The association is made possible by a calibration process of, for example, capturing, in advance, an image of a reference object, the shape of which is known. The three-dimensional shape of the observation site may be acquired based on the process of generating the above-described narrow range image having a great depth of field and the above-described focal point position information.

If the plurality of images, captured by continuous image capturing in order to generate a narrow range image having an expanded depth of field, are blurred, the amount of contrast may, for example, exhibit the maximum value a plurality of times in the process of (2). In this case, the measured three-dimensional shape may be distorted or may have noise. According to one or more embodiments of the present invention, the three-dimensional shape is measured based on the narrow range image having the blur corrected. Therefore, the above-described situation of the noise or the like may be resolved, and the three-dimensional shape may be measured with higher precision.

According to one or more embodiments of this invention, an image of the narrow range image that is clear and has a great depth of field is captured by the narrow range image capturing portion, and thus the three-dimensional shape of the image-captured site may be measured with high precision.

In one or more embodiments of the present invention, the observation site may be a desired site in an oral cavity, and the three-dimensional position detector may detect the three-dimensional position of the observation site by detecting, in the wide range image, a plurality of colored sites, colored by occlusion paper, on a surface of a tooth in the oral cavity.

According to one or more embodiments of this invention, the characteristic points may be formed in the oral cavity. Therefore, for example, it is not needed to provide a separate member acting as a characteristic point such as a ball marker or the like. Thus, the pain of the patient caused by such a separate member is decreased while the three-dimensional position may be detected with high precision.

In one or more embodiments of the present invention, the image display portion may be of a head-mountable type mountable on the head of an observer.

The image display portion of the head-mountable type may be any of various types that allows at least the eyepieces to be attached to the head, such as a head gear type, a helmet type, a sun visor type, a band type, or a type attachable by a clip to the frame of general eyeglasses normally used by the observer for correcting the eyesight or the like.

According to one or more embodiments of this invention, the observer may observe the observation site at any position with no restriction on the movement of the head while the narrow range image having the blur corrected is displayed.

One or more embodiments of the present invention is directed to an observation unit including the above-described observation device; and a support supporting at least the narrow range image capturing portion of the observation device.

According to one or more embodiments of this invention, the observer may observe the observation site by the observation device supported by the supporter with no load on the head of the observer while the narrow range image having the blur corrected is displayed.

The supporter may be, for example, a support arm extending from a ceiling, a wall, a floor, a stand, a wagon, a rack, a medical care table, a spittoon table, a medical robot, another medical device or the like.

In one or more embodiments of the present invention, the support may allow at least the narrow range image capturing portion, supported by the support, of the observation device to move with respect to the observation site.

The support may be, for example, a support arm including movable joints. In this case, the observer may bend the joints to move the support, namely, move the supported observation device, with respect to the observation site, and thus may observe the observation site from a desired position.

According to one or more embodiments of this invention, the observation may be made after the support is located at an appropriate position with respect to the observation site. Thus, the observation may be made in more detail.

In one or more embodiments of the present invention, the observation unit may further include a display device displaying at least the narrow range image having the blur corrected.

The display device may be provided at a position different from the position of the main body of the observation main body, for example, on the support, the wall, the ceiling or the like, or a plurality of display devices may be provided.

According to one or more embodiments of this invention, even in the case where the observer moves to any of various positions or in the case where there are a plurality of observers, the narrow range image having the blur corrected may be displayed for observation from various viewing positions by the display device different from the image display portion. In, for example, dental care, the display device may be set at a position viewable from the patient, who is an observation subject. This is effective to explain the situation of the care to the patient or to obtain informed consent.

In one or more embodiments of the present invention, the display device may be of a head-mountable type mountable on the head of an observer.

The image display device of the head-mountable type may be any of various types that allows at least the eyepieces to be attached to the head, such as a head gear type, a helmet type, a sun visor type, a band type, an eyeglass type, or a type attachable by a clip to the frame of general eyeglasses normally used by the observer for correcting the eyesight or the like.

According to one or more embodiments of this invention, the observer may observe the observation site with no restriction on the movement of the head while the narrow range image having the blur corrected is displayed.

Advantageous Effects

One or more embodiments of the present invention provides an observation device, an observation unit and an observation method allowing an observation site of a small range to be precisely observed while suppressing the blur.

BRIEF DESCRIPTION OF DRAWINGS

FIGS. 9A and 9B show schematically shows display screens.

DETAILED DESCRIPTION

Hereinafter, a magnifying glass 1 according to one or more embodiments of the present invention will be described with reference to FIGS. 1A and 1B through FIG. 14.

Figure 1A:
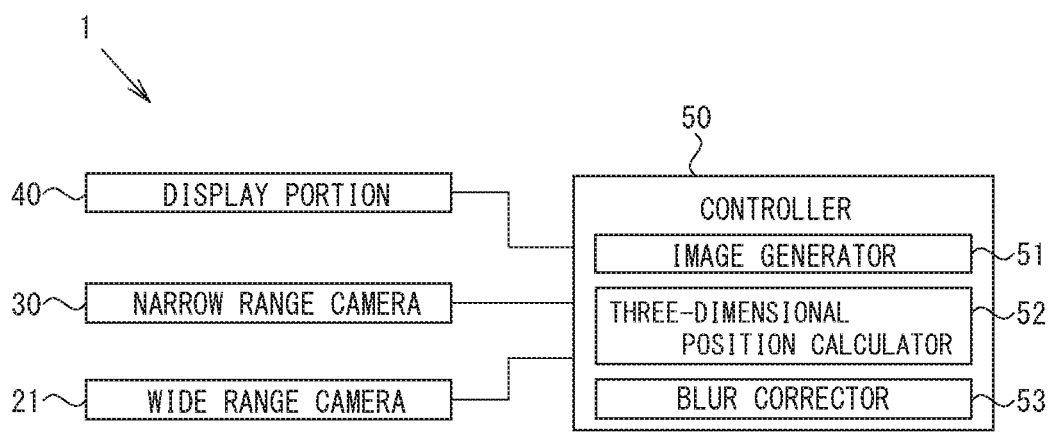
FIGS. 1A and 1B show structures of a magnifying glass.
Figure 1B:
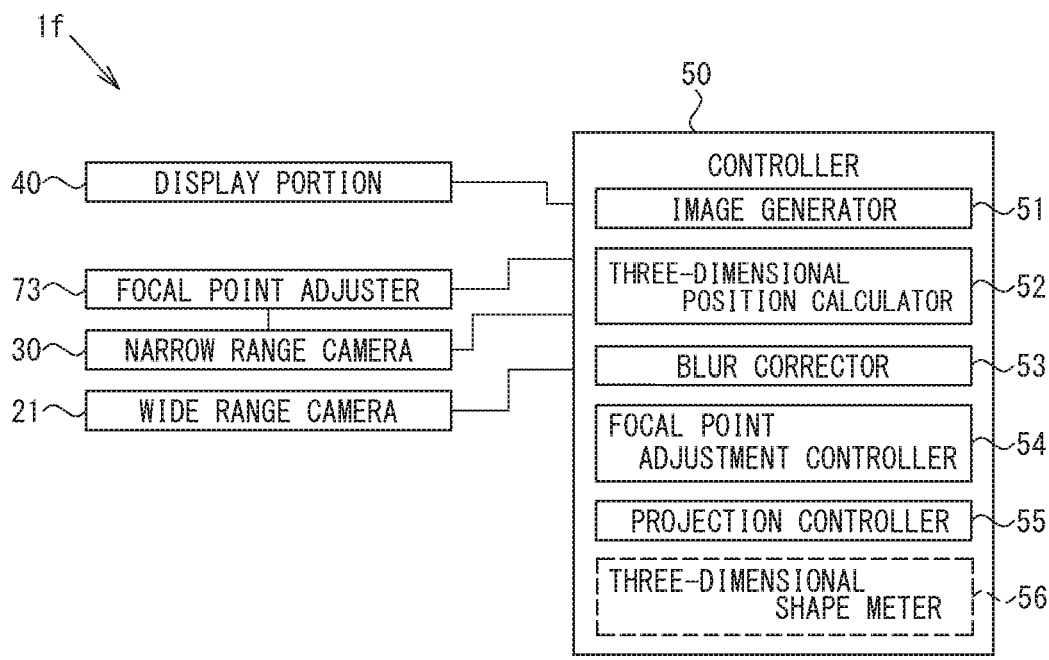
Figure 2:
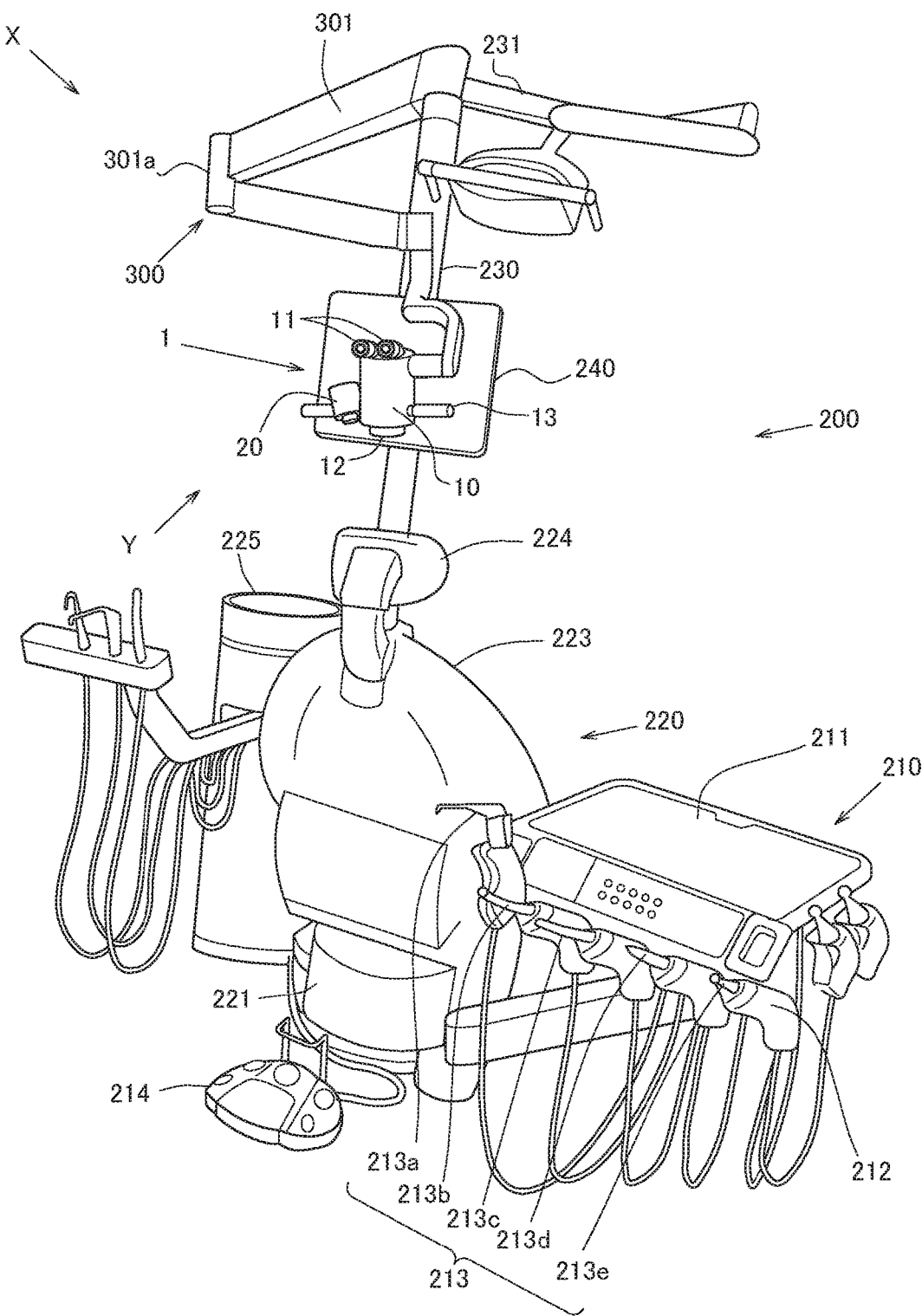
FIG. 2 is a schematic perspective view of a care unit.
Figure 3:
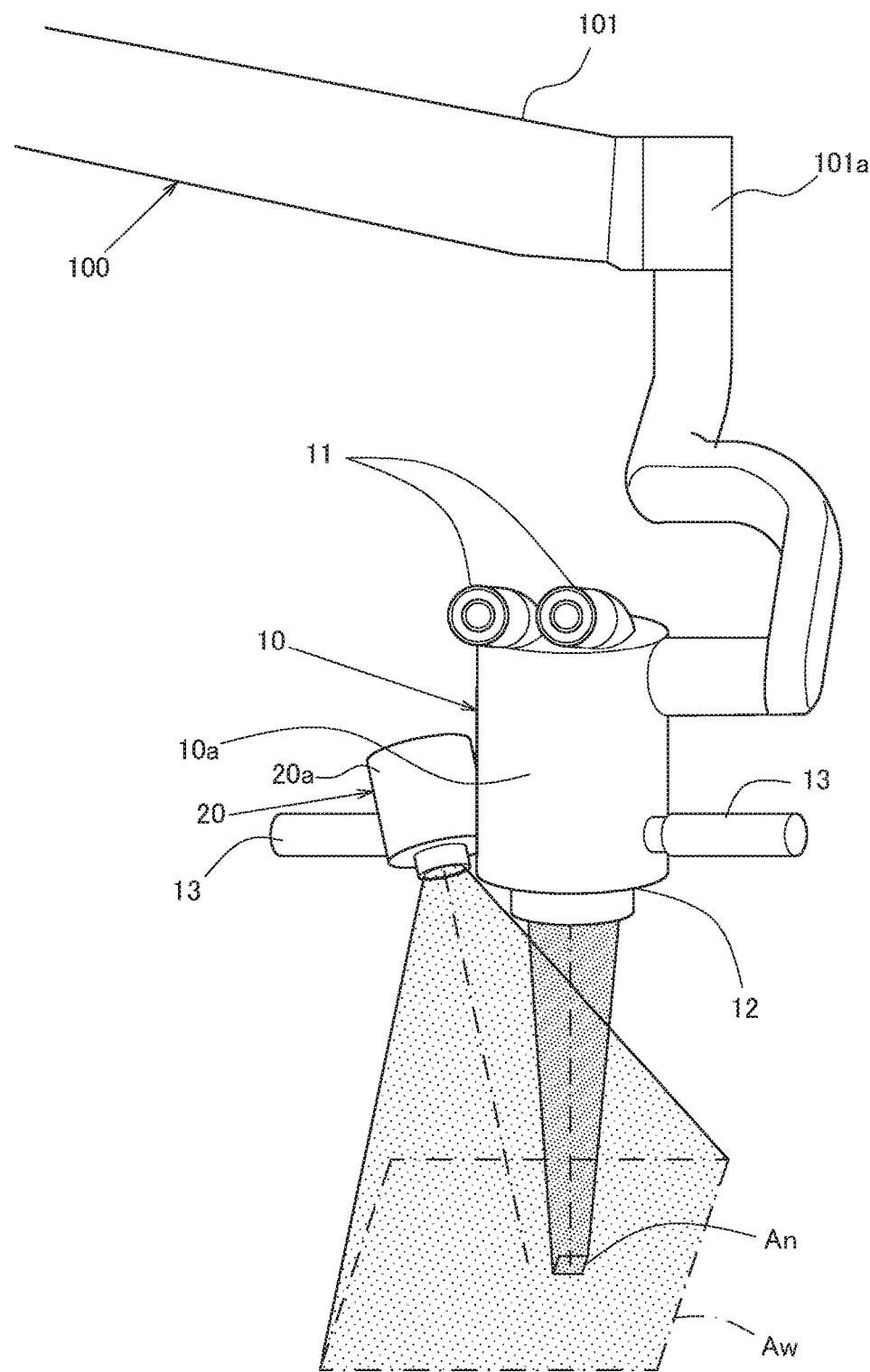
FIG. 3 is a schematic enlarged perspective view of the magnifying glass.
Figure 10:
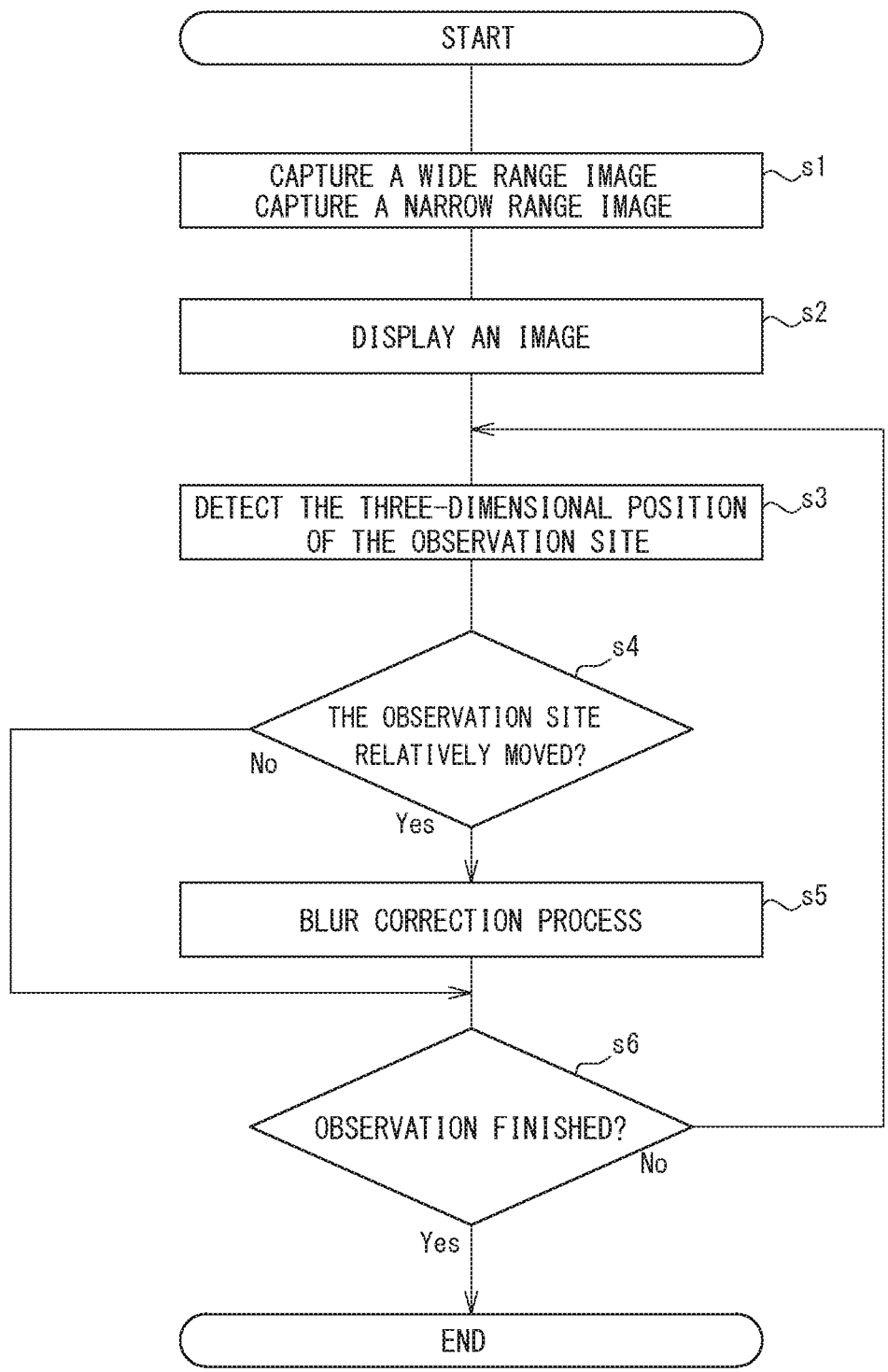
FIG. 10 is a flowchart of an observation method performed by use of the magnifying glass.
Figure 11:
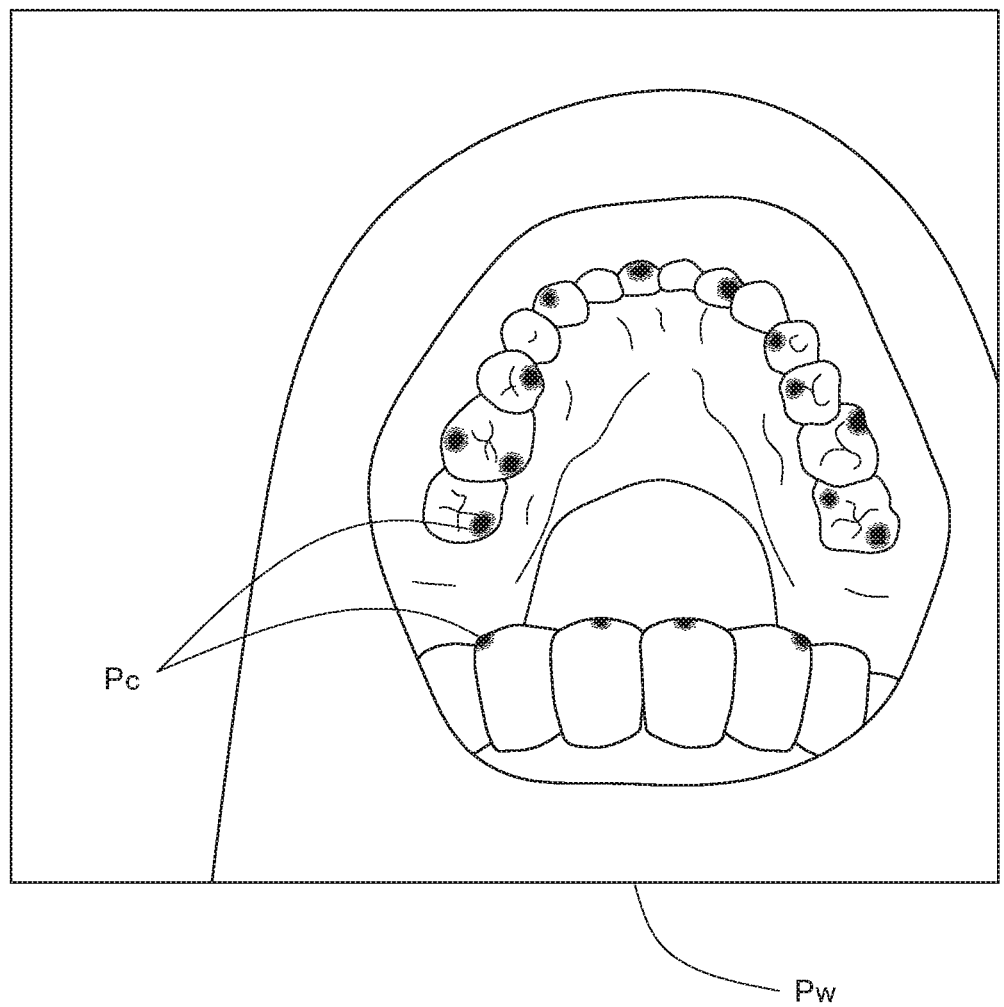
FIG. 11 shows a marking method for measuring a three-dimensional position of an observation site.

FIGS. 1A and 1B provide a structure the magnifying glass 1 and a structure of an omnifocal magnifying glass 1*f*. FIG. 2 is a schematic perspective view of a care unit X. FIG. 3 is a schematic enlarged perspective view of the magnifying glass 1. FIG. 4 through FIGS. 8A and 8B each show a wide range optical system W and a narrow range optical system N. FIGS. 9A and 9B show schematic views of a display image P. FIG. 10 is a flowchart of an observation method performed by use of the magnifying glass 1. FIG. 11 shows a marking method for measuring a three-dimensional position of an observation site.

Figure 12:
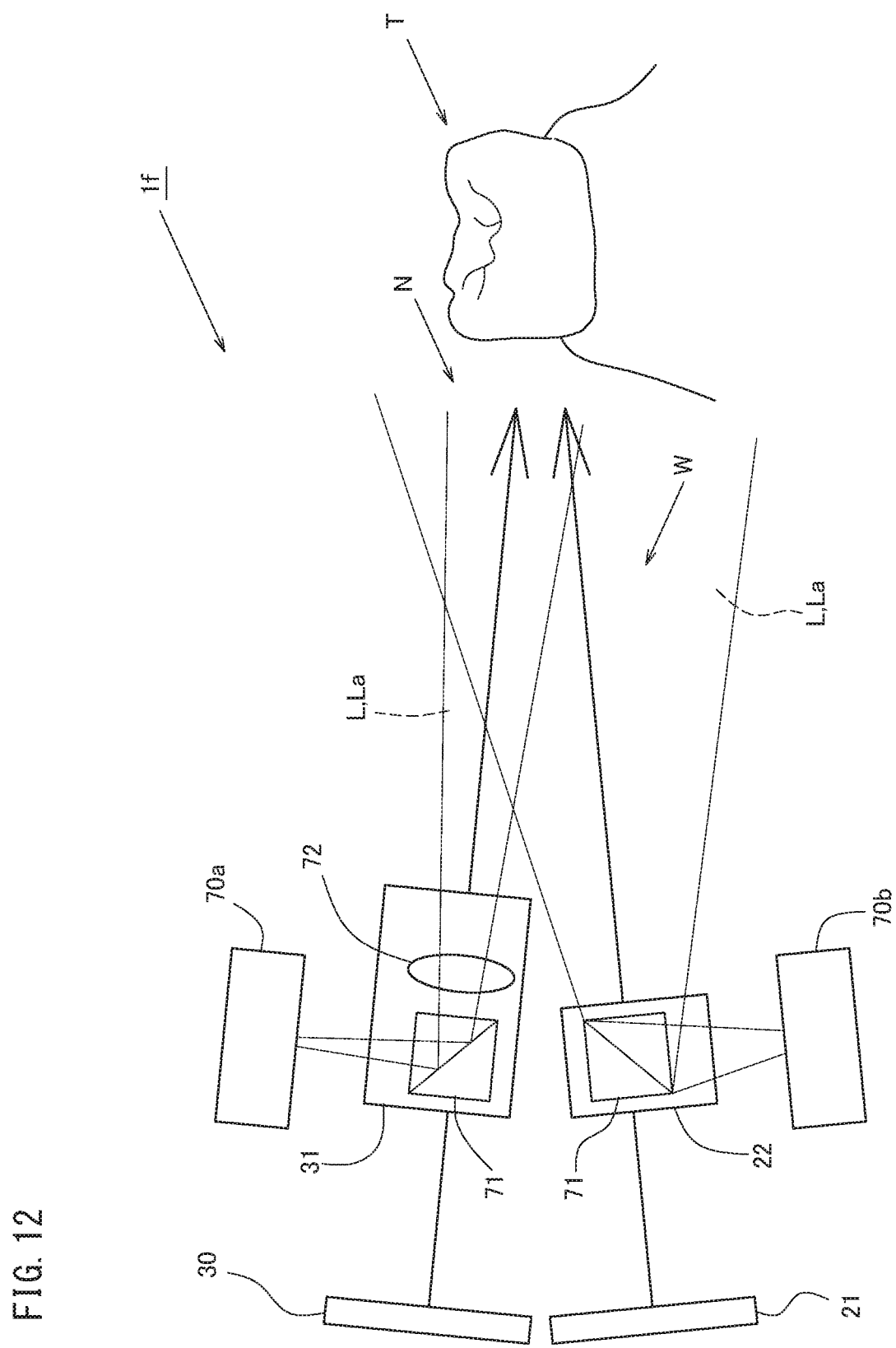
FIG. 12 is a schematic view of an omnifocal magnifying glass.
Figure 13:
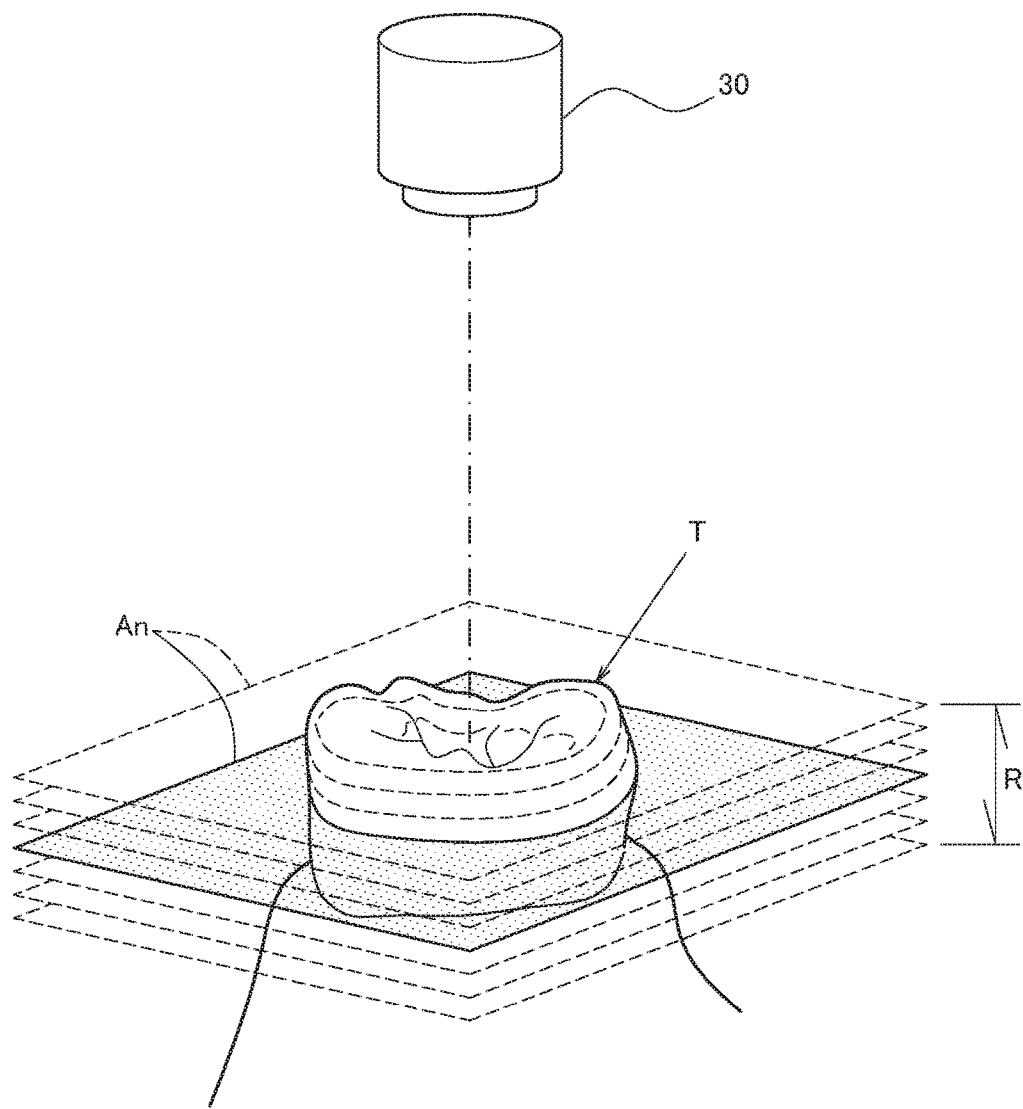
FIG. 13 schematically shows a state of observation performed by use of the omnifocal magnifying glass.
Figure 14:
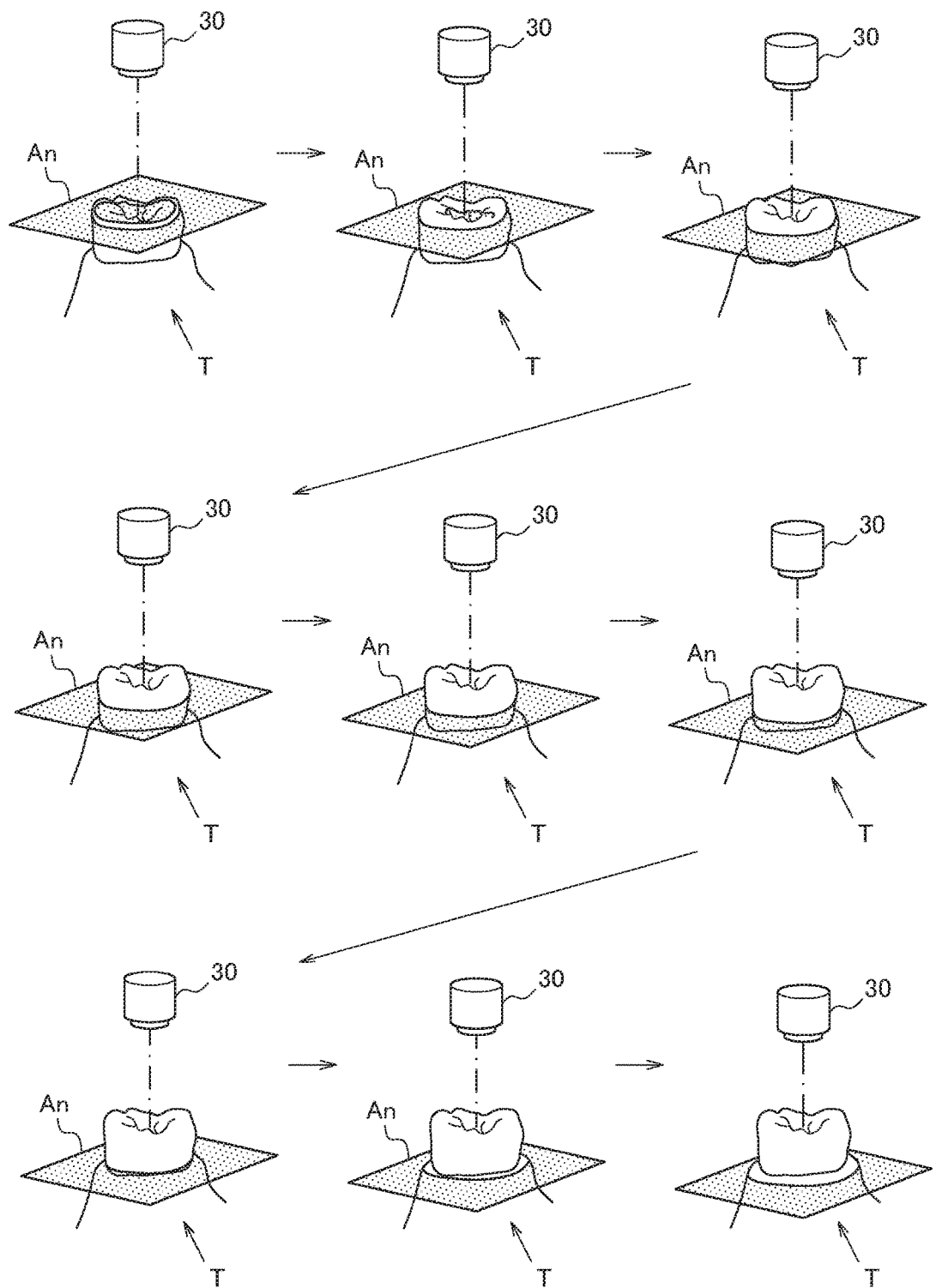
FIG. 14 shows, in detail, an omnifocal observation method performed by use of the omnifocal magnifying glass.

FIG. 12 is a schematic view of the omnifocal magnifying glass 1*f*. FIG. 13 is a schematic view of a state of observation performed by use of the omnifocal magnifying glass 1*f*. FIG. 14 shows, in detail, an omnifocal observation method performed by use of the omnifocal magnifying glass 1*f*.

Figure 4:
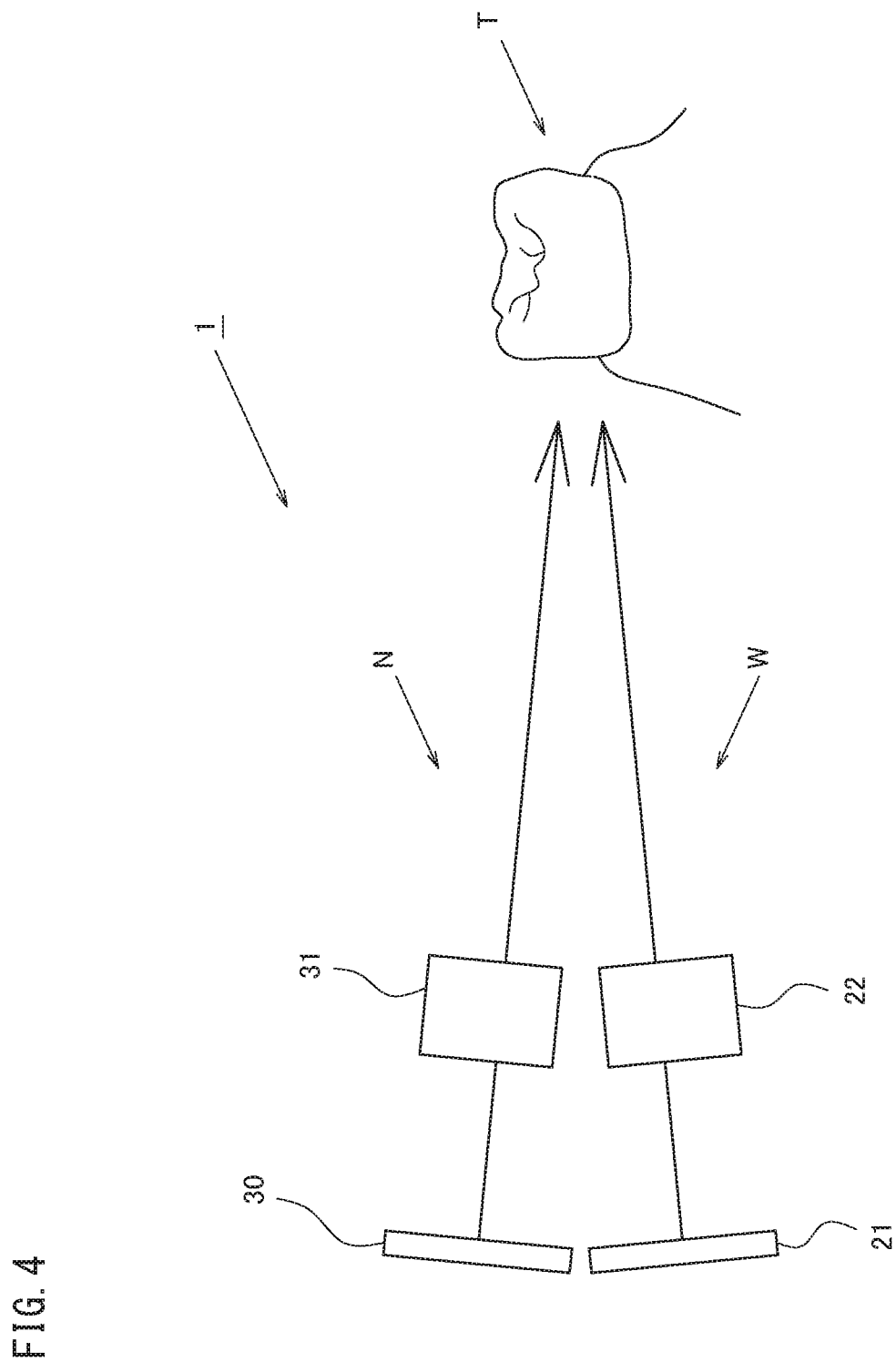
FIG. 4 schematically shows an optical structure of the magnifying glass.

This will be described in detail. FIG. 1A is a block diagram showing the structure of the magnifying glass 1. FIG. 1B is a block diagram showing the structure of the omnifocal magnifying glass 1*f*. FIG. 4 is a schematic view showing an optical structure of the magnifying glass 1 including the narrow range optical system N and the wide range optical system W provided separately from each other.

Figure 5A:
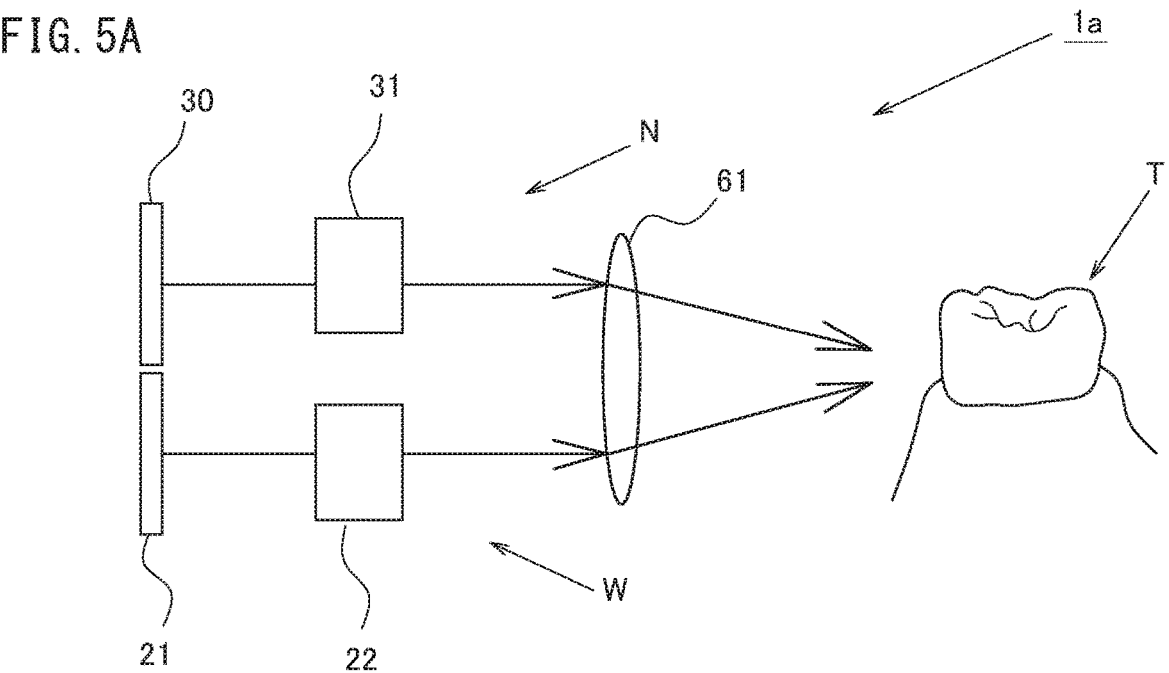
FIGS. 5A and 5B show a wide range optical system and a narrow range optical system.
Figure 5B:
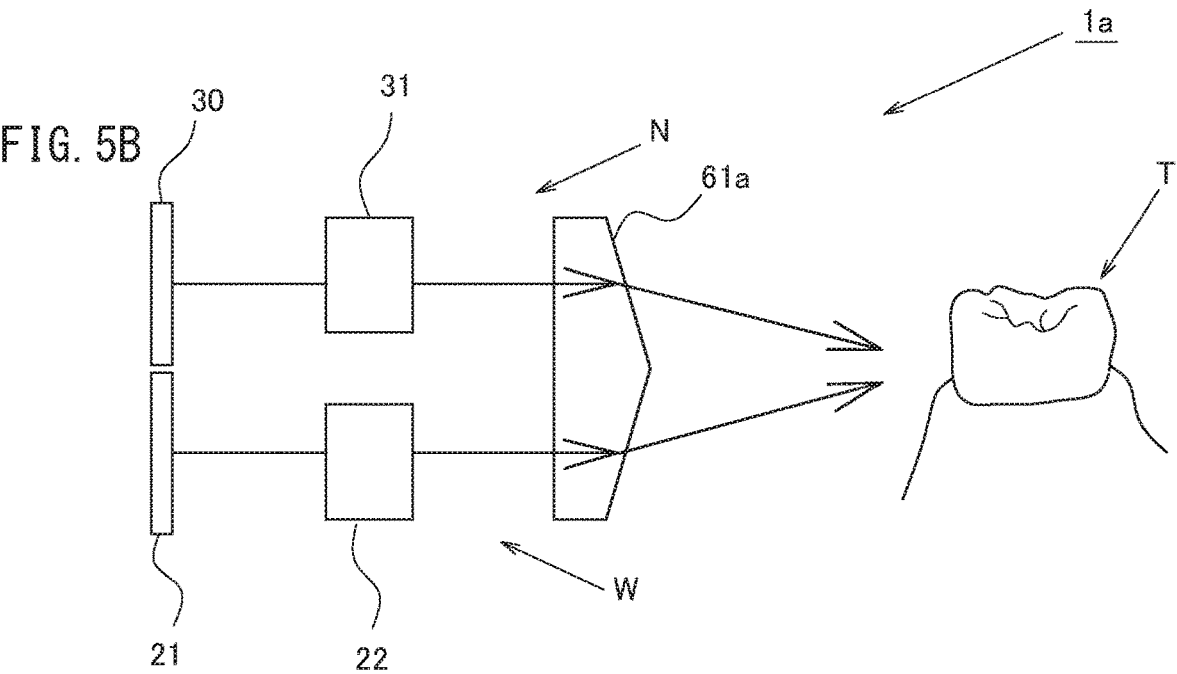
Figure 6A:
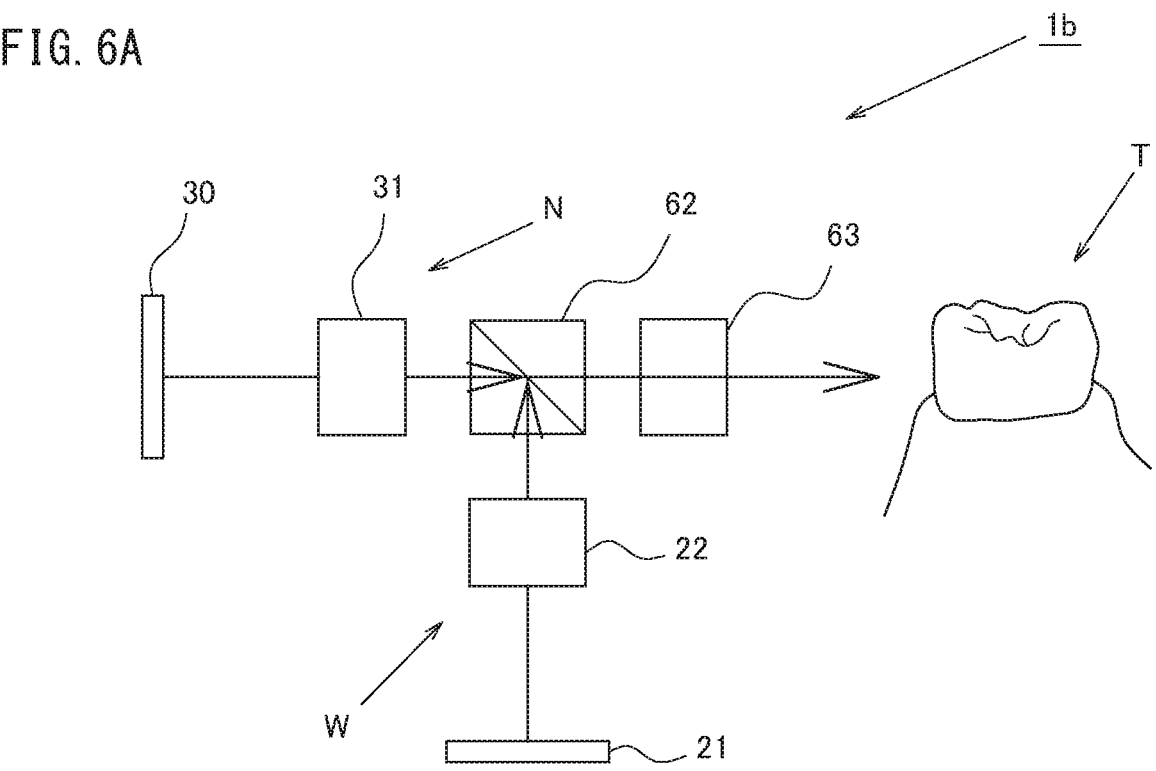
FIGS. 6A and 6B show a wide range optical system and a narrow range optical system.
Figure 6B:
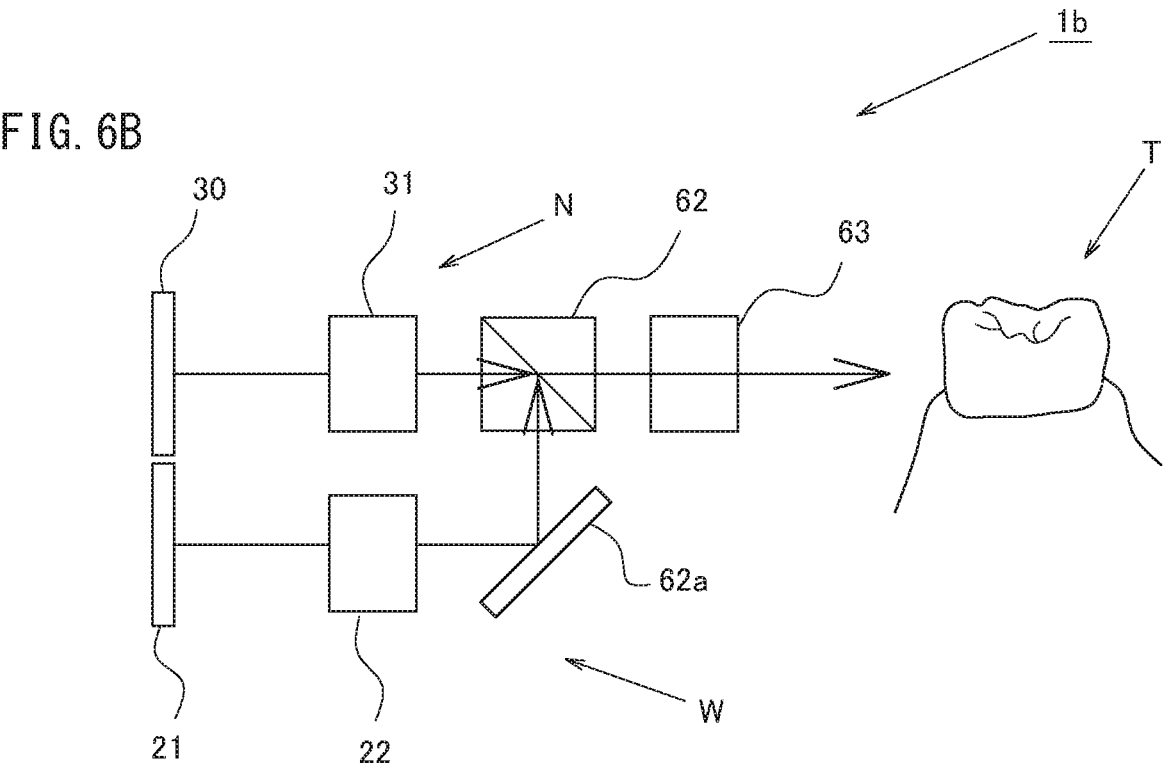

FIG. 5A is a schematic view showing an optical structure of a magnifying glass 1*a* in which the narrow range optical system N and the wide range optical system W provided separately from each other are made common at a tip by a common lens 61, which provides a common optical path. FIG. 5B is a schematic view showing an optical structure of a magnifying glass 1*a* in which the narrow range optical system N and the wide range optical system W provided separately from each other are made common at a tip by a wedge plate 61*a*, which provides a common optical path. FIG. 6A and FIG. 6B are each a schematic view showing an optical structure of a magnifying glass 1*b* in which the narrow range optical system N and the wide range optical system W are made common at a tip by a beam splitter 62, which provides a common optical path.

Figure 7A:
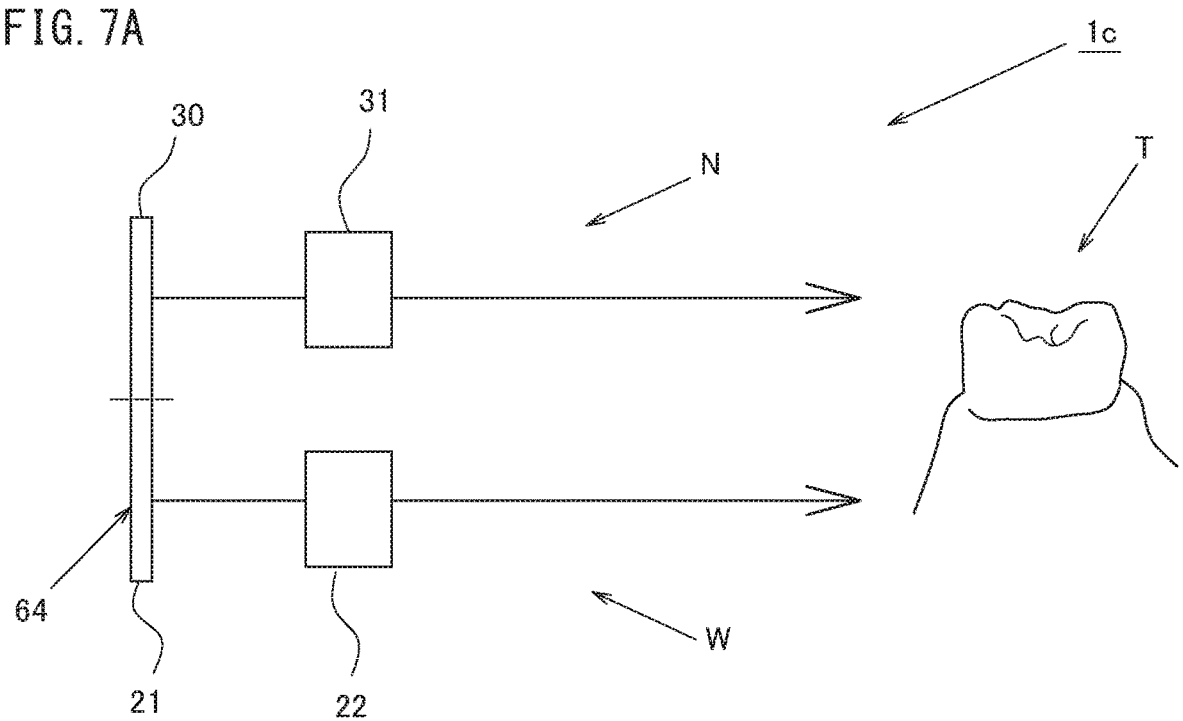
FIGS. 7A and 7B show a wide range optical system and a narrow range optical system.
Figure 7B:
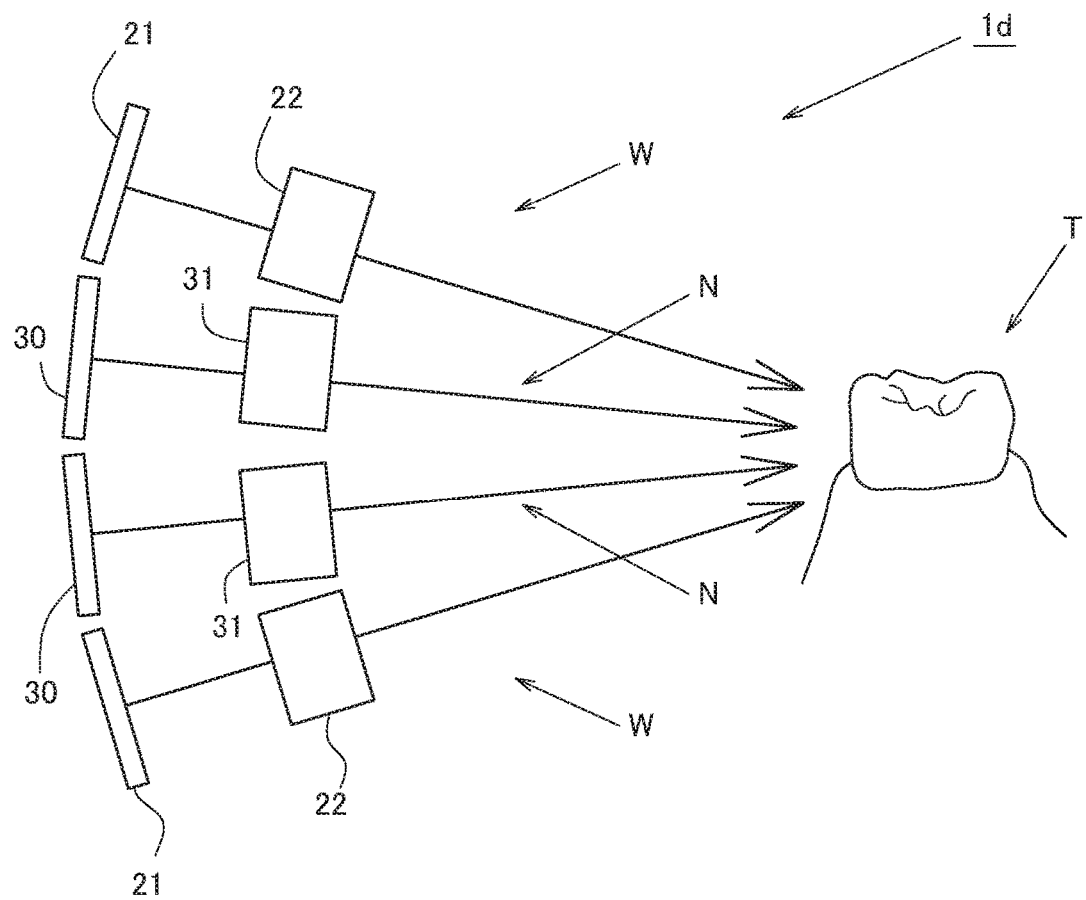

FIG. 7A is a schematic view showing an optical structure of a magnifying glass 1*c* in which the narrow range optical system N and the wide range optical system W are provided in a common image sensor 64. FIG. 7B is a schematic view showing an optical structure of a magnifying glass 1*d* in which two combinations each including the narrow range optical system N and the wide range optical system W are provided. The narrow range optical system N and the wide range optical system W in each of the combinations are provided separately from each other.

Figure 8A:
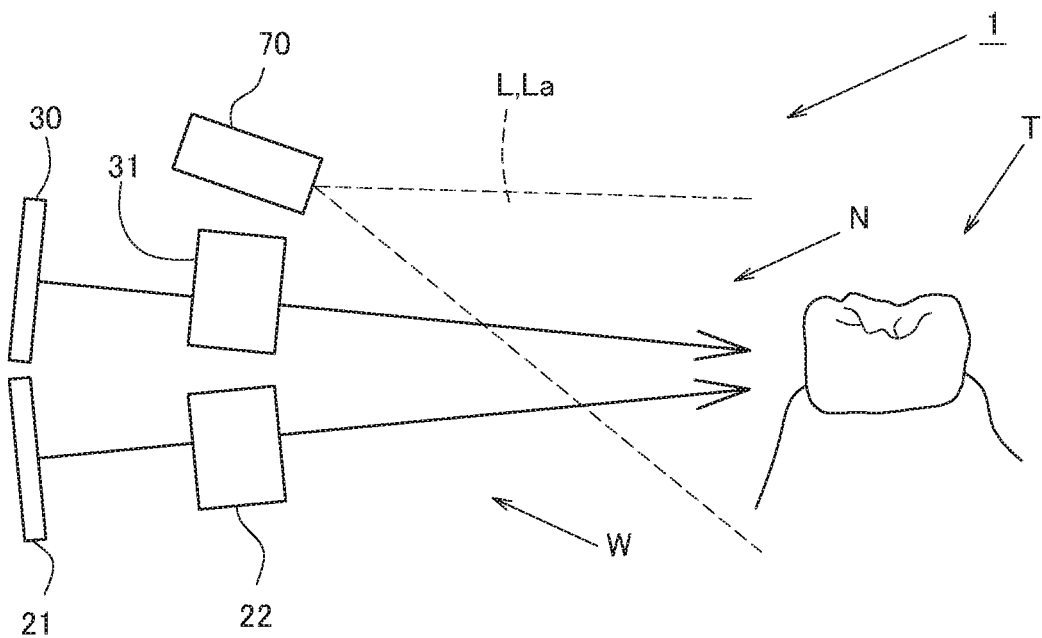
FIGS. 8A and 8B show a wide range optical system and a narrow range optical system.
Figure 8B:
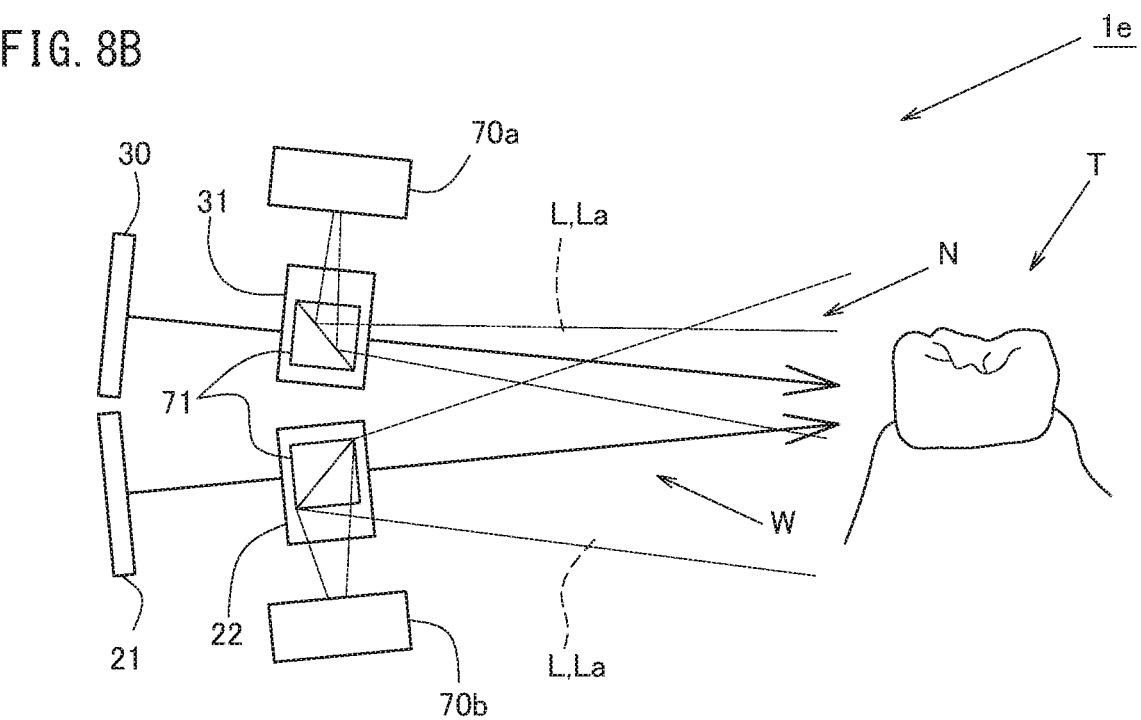

FIG. 8A is a schematic view showing an optical structure of a magnifying glass 1 in which a projector 70 is provided commonly for the narrow range optical system N and the wide range optical system W provided separately from each other. FIG. 8B is a schematic view showing an optical structure of a magnifying glass 1*e* in which projectors 70 are respectively provided for the narrow range optical system N and the wide range optical system W provided separately from each other. FIG. 14 schematically shows steps of observing a tooth T, which is an observation target, by an omnifocal observation method by use of the omnifocal magnifying glass 1*f*.

The care unit X includes a dental care device 200 shown in FIG. 2 and an observation unit Y usable together with the magnifying glass 1, which corresponds to an observation device.

As shown in FIG. 2, the dental care device 200 includes a tool table 210 including care tools 213 (213*a* through 213*e*) and a care chair 220, on which a patient as an operation target is to sit to be treated.

The tool table 210 includes a table 211 pivotably attached to the care table 220 via an arm. Tool holders 212 are provided to the front of the table 211. Care tools 213 (213*a* through 213e) including cutting tools such as an air turbine handpiece, a micromotor handpiece and the like, a scaler, a three-way syringe, a vacuum syringe and the like are detachably attached to the tool holders 212.

The care tools 213 are driven as being connected with a water supply, an air supply or an air absorber. Mechanisms of these components are known and will not be described in detail.

A foot controller 214, on which various operation commands are to be input, is provided. A mechanism of the foot controller 214 is known and will not be described in detail.

As shown in FIG. 2, the care chair 220, on which the patient is to sit, includes a sitting seat located on a base 221 in an elevatable manner, an inclinable back seat 223 provided to the rear of, and coupled with, the sitting seat, and an inclinable head rest 224 provided to the rear of, and coupled with, a top end of the back seat 223. A sitting seat elevator, a back seat incliner, and a head rest incliner are provided to control the sitting seat, the back seat 223 and the head rest 224 to optimal positions in accordance with the care state. The sitting seat elevator, the back seat incliner and the head rest incliner are driven by a hydraulic cylinder, an electric motor and the like controlled to operate by the foot controller 214.

The care chair 220 is provided with a spittoon 225 and a treating stand pole 230. An arm 231 is branched from the treating stand pole 230 at the middle and protrudes to be pivotable, and a support arm 300 described below is provided at a top end of the treating stand pole 230.

The treating stand pole 230 is provided with the magnifying glass 1 and a monitor 240 included in the observation unit Y.

The spittoon 225 includes a water supply plug usable to supply water when the patient needs to wash out his/her oral cavity and a saliva bowl. On the back of the patient or in the vicinity of the belly of the patient, a connector (not shown) is provided and is connected with an electrical pathway, a hydraulic pathway, an air pathway or the like provided in the care chair 220.

The magnifying glass 1 is supported by the support arm 300 (corresponding to a support) that is positionally adjustable. The support arm 300 and the magnifying glass 1 are included in the observation unit Y.

The support arm 300 is provided to be pivotable with respect to the top end of the treating stand pole 230 attached to the care chair 220. The support arm 300 is a multi-joint arm including a plurality of arms 301 coupled with each other at a plurality of joints 301a so as to be movable. The support arm 300 is capable of moving the magnifying glass 1 attached to a tip thereof to a desired position.

Instead of being provided at the treating stand pole 230 attached to the care chair 220, the support arm 300 may extend from a ceiling, a wall or a floor, or may be provided on a stand, a wagon or a rack separate from the treating stand pole 230. Alternatively, the support arm 300 may extend from a medical care table, a spittoon table, a medical robot, another medical device or the like.

The care unit X includes the magnifying glass 1 and the dental care device 200 having such a structure. As shown in FIG. 1A and FIG. 3, the magnifying glass 1 includes a magnifying glass main body 10 and a wide range image capturing device 20 provided to be along the magnifying glass main body 10.

The wide range image capturing device 20 includes a wide range camera 21 and a wide range optical path 22 (see FIG. 4) in a casing 20a secured to a casing 10a of the magnifying glass main body 10. The wide range camera 21 includes an image sensor. The wide range optical path 22 includes a lens or the like that captures an image of a wide range including the tooth T, which is an observation target.

An image captured by the wide range camera 21 is of a resolution lower than a resolution of an image captured by a narrow range camera 30 described below. However, as shown in FIG. 3, the wide range camera 21 is located to be capable of capturing, by the wide range optical path 22, a wide image capturing range Aw, which is a wide range including a narrow image capturing range An to be captured by the narrow range camera 30. The wide range camera 21 is connected with a controller 50 by a communicator (not shown).

The wide range camera 21 includes a three-dimensional camera capable of capturing an image of a three-dimensional position of the tooth T or the wide image capturing range Aw.

The wide range camera 21 shown in FIG. 4 is, for example, a single lens-type three-dimensional camera, and may be a three-dimensional camera adopting a known three-dimensional measurement principle such as, for example, trigonometry, focusing, Time of Flight, RGB-D (Distance) camera, light field camera or the like.

Alternatively, a three-dimensional measurement device different from the wide range camera 21 may be provided inside or outside the wide range image capturing device 20. In this case, three-dimensional position information on the tooth T or the wide image capturing range Aw is acquired by use of such a three-dimensional measurement device to provide a three-dimensional captured image. Still alternatively, a camera having multiple optical paths may be used to provide a three-dimensional image based on images captured at three or more angles. Such a camera is, for example, a two-lens camera (stereo camera), a multi-lens camera including three or more lenses, or the like.

In FIG. 3, the wide range camera 21 is shown as having a single casing 21a. Alternatively, in the case of being a three-dimensional camera of a two-lens type or a multi-lens type, the wide range camera 21 may include a plurality of cameras in one casing 21a, or may include a casing for each of the plurality of cameras.

In FIG. 3, the casing 20a is provided separately from the casing 10a of the magnifying glass main body 10. Instead, the wide range camera 21 may be provided in the casing 10a of the magnifying glass main body 10.

The casing 10a of the magnifying glass main body 10 is provided with eyepieces 11 and an objective portion 12. The magnifying glass main body 10 includes, in the casing 10a, the narrow range camera 30 located in correspondence with the objective portion 12, a narrow range optical path 31 (see FIG. 4) including, for example, a lens that captures an image of the tooth T at high precision, an image display portion 40 located in correspondence with the eyepieces 11, and the controller 50.

The casing 10a is provided with a handle 13 to be held by the observer to move the magnifying glass 1 to a desired position, namely, to move the joint 301a of each of the arms included in the support arm 300, which is a multi-joint arm. The casing 10a may be provided with a start switch that starts the magnifying glass 1, an adjuster that adjusts the position of the eyepieces 11 or the like (not shown), in addition to the above-described components.

The narrow range camera 30 includes an image sensor. The observation range, of the narrow range camera 30, defined by the narrow range optical path 31 located in correspondence with the objective portion 12 is narrow (narrow image capturing range An) as shown in FIG. 3.

However, an image captured by the narrow range camera 30 has a resolution higher than a resolution of an image captured by the wide range camera 21 described above. Namely, the narrow range camera 30 may capture, by the narrow range optical path 31, an image of the tooth T at a high resolution for observation.

The narrow range camera 30 may include a three-dimensional camera that captures an image of the tooth T three-dimensionally. In this case, the three-dimensional camera may be a two-lens type (binocular type) using parallax of the left and right eyes for observation, or a single-lens type. The narrow range camera 30 is connected with the controller 50 described below by a communicator (not shown).

The image display portion 40 is located in correspondence with the eyepieces 11 as described above, and may display an image of the tooth T captured by the narrow range camera 30. Therefore, the observer may observe an image of the tooth T, captured by the narrow range camera 30 and displayed on the image display portion 40, via the eyepieces 11.

The image display portion 40 may be a liquid crystal display, an organic EL display or the like that displays captured image information, or may be, for example, of a type that projects a video on the screen, of a type that writes a video on the retina of the observer by laser scanning, or of a type that is capable of displaying a three-dimensional image captured by a three-dimensional camera.

The image display portion 40 may be provided for each of the left and right eyepieces 11, namely, for the eyepiece 11 for the left eye and for the eyepiece 11 for the right eye. Alternatively, the image display portion 40 may be provided commonly to, and viewed via, the left and right eyepieces 11.

The image display portion 40 is connected with the controller 50 by a communicator (not shown).

The controller 50 includes a CPU, a ROM, a RAM and the like, and acts as an image generator 51, a three-dimensional position calculator 52, a blur correction processor 53 and the like.

The image generator 51 generates an image to be displayed on the image display portion 40 based on an image captured by at least the narrow range camera 30. For example, the image generator 51 allows a display image P shown in FIG. 9A to be displayed on the image display portion 40. The display image P shown in FIG. 9A includes a narrow range observation image display Pn displaying an image captured by the narrow range camera 30 and a wide range observation image display Pw displaying an image captured by the wide range camera 21. The narrow range observation image display Pn and the wide range observation image display Pw are displayed side by side.

The wide range observation image display Pw has a low resolution but has a larger display region than the narrow range observation image display Pn. The wide range observation image display Pw may display, for observation, a wide range including the tooth T, for example, the entirety of the dental arch.

By contrast, the narrow range observation image display Pn has a high resolution but has a smaller display region than the wide range observation image display Pw. The narrow range observation image display Pn displays only the tooth T and the vicinity thereof for observation.

In FIG. 9A, the narrow range observation image display Pn and the wide range observation image display Pw are displayed side by side. Alternatively, only the narrow range observation image display Pn may be displayed as the display image P, and may be switched with the wide range observation image display Pw, by a predetermined operation made by use of the foot controller 214 or the like or automatically. Still alternatively, after the narrow range observation image display Pn and the wide range observation image display Pw are displayed side by side, only the narrow range observation image display Pn may be displayed and then switched to the wide range observation image display Pw.

The image displays Pw and Pn may be changed in the display size, the display concentration or the like by an operation made on an input device such as the foot controller 214, a mouse or the like. The image displays Pw and Pn may be displayed as overlapping each other partially or entirely.

The three-dimensional position calculator 52 calculates a three-dimensional position of the tooth T and also detects a relative positional change based on the image of the wide image capturing range Aw (based on a wide range image) captured by the wide range camera 21. The three-dimensional position calculator 52 calculating the three-dimensional position of the tooth T may calculate an absolute three-dimensional position or may calculate at least a relative three-dimensional position with respect to the wide range camera 21 integral with the narrow range camera 30.

Specifically, the three-dimensional position calculator 52 compares the wide range image currently captured and at least one wide range image captured at a timing before the current timing, among wide range images captured continuously. Then, the three-dimensional position calculator 52 finds what type of motion is made by a characteristic site (characteristic point) in the captured images by use of a technique such as template matching, characteristic point matching or the like, and thus detects a three-dimensional position at each of the timings and a change amount of the three-dimensional position from the immediately previous timing.

It is sufficient that there are at least three characteristic points described above, and the characteristic points may be of the dental arch including the tooth T, a ball marker rigidly attached to the dental arch, or the like. In the case where the wide range camera 21 is a stereo camera including two cameras, two-dimensional characteristic points in an image captured by each of the two cameras in the wide range camera 21 may be processed by stereo matching to calculate the three-dimensional position.

Alternatively, the wide range camera 21 may be a three-dimensional camera. In this case, a three-dimensional surface shape of the dental arch may be calculated. The three-dimensional characteristic points in the three-dimensional surface shape thus calculated may be adopted.

In the case where the oral cavity of a patient, whose posture is secured as lying on his/her back as in the dental care, is observed generally from above by the magnifying glass 1, a blur in a direction other than an up-down direction (the up-down direction is a straight direction from the tooth T toward the magnifying glass 1) inhibits the observation more often than a blur in the up-down direction.

In this case, the relative three-dimensional position calculated by the three-dimensional position calculator 52 may be approximated, with no problem, to a two-dimensional relative position in consideration of only the direction other than the up-down direction, with a movement of the relative position in the up-down direction being ignored. This may alleviate the calculation load on the three-dimensional position calculator 52. In this case, only two or smaller number of characteristic points may be needed.

The blur correction processor 53 detects a change in the three-dimensional position of the tooth T calculated by the three-dimensional position calculator 52. Based on the detected change in the three-dimensional position, the blur correction processor 53 corrects a blur caused, by the change in the relative three-dimensional position, to the image of a high resolution captured by the narrow range camera 30.

According to an example of method for correcting the blur caused to the narrow range image of high precision captured by the narrow range camera 30 based on the detected change in the three-dimensional position of the tooth T, the narrow range image may be subjected to an image process such as, for example, a parallel movement of a pixel value, a rotational movement of a pixel value, or enlargement/reduction of a pixel value.

According to another method for correcting the blur, the entirely of the magnifying glass main body 10 may be moved in such a direction as to eliminate the change in the relative three-dimensional position such that the narrow range image is not blurred, or a part of the narrow range camera 30 and a part of the narrow range optical path 31 may be moved in such a direction as to eliminate the change in the relative three-dimensional position such that the narrow range image is not blurred. Alternatively, the movement of the entirety of the magnifying glass main body 10 and the movement of a part of the narrow range camera 30 and a part of the narrow range optical path 31 may be combined. Still alternatively, the above-described image process and the movement of the narrow range camera 30 or the like may be combined to correct the blur.

The entirety of the magnifying glass main body 10, or a part of the narrow range camera 30 and a part of the narrow range optical path 31, may be moved, for example, by any of the following methods: according to one method, an actuator is used to mechanically move the magnifying glass main body 10 or at least a part of the narrow range camera 30 and at least a part of the narrow range optical path 31; and according to another method, a variable lens, a variable prism, a spatial light modulator or the like that is variable in the refractive index or the shape by electric control is used to optically move the optical axis.

As shown in FIG. 4, the magnifying glass 1 including the above-described components includes the wide range optical system W including the wide range camera 21 and the wide range optical path 22 and the narrow range optical system N including the narrow range camera 30 and the narrow range optical path 31. The wide range optical system W and the narrow range optical system N are provided separately from each other.

The tooth T may be observed by use of the magnifying glass 1 as shown in the flowchart in FIG. 10. First, an image of the tooth T is captured by the narrow range optical system N and the wide range optical system W (step s1), and display images generated based on the captured images are displayed on the image display portion 40 (step s2).

Specifically, an image of the tooth T via the narrow range optical path 31 is captured by the narrow range camera 30 of the narrow range optical system N, and an image of the tooth T via the wide range optical path 22 is captured by the wide range camera 21 of the wide range optical system W (step s1).

In this step, the narrow range camera 30 captures an optical image of a narrow range including the tooth T (narrow range image) at a high resolution, and the wide range camera 21 captures an optical image of a wide range including the tooth T (wide range image) at a low resolution. After detecting the captured images, the narrow range camera 30 and the wide range camera 21 output the captured image information to the image generator 51 of the controller 50 connected therewith via a communicator (not shown). A display image such as, for example, the display image P is generated by the image generator 51 and is displayed on the image display portion 40 connected with the controller 50 (step s2).

The three-dimensional position calculator 52 calculates a three-dimensional position of the tooth T based on the wide range image detected by the wide range camera 21 (step s3). In this step, when a relative movement of the tooth T with respect to the wide range camera 21 is detected (step s4: Yes), the blur correction processor 53 performs a blur correction on the narrow range image, captured by the narrow range camera 30 and blurred by the relative movement of the tooth T, to address the blur (step s5). A display image obtained as a result of the blur correction is displayed on the image display portion 40 as the narrow range observation image display Pn. This is repeated until the observation is finished (step s6: No). When the observation is finished (step s6: Yes), the flow is finished.

The operation of correcting the blur may be switched on or off by an operation on the input device such as the foot controller 214, the mouse or the like.

For example, while the observer holds the handle 13 to move the magnifying glass 1 to a desired observation position, it is advantageous not to perform a blur correction because the relative three-dimensional position may be changed by an amount exceeding the correction limit.

Instead of being switched on or off by the above-described manual method, the operation of correcting the blur may be automatically switched on or off in accordance with a parameter such as a vibration frequency, a vibration amplitude or the like calculated based on a history of the change amount of the relative three-dimensional position.

As described above, the magnifying glass 1 usable to capture an image of the tooth T with the cameras 30 and 21 to observe the tooth T includes the narrow range camera 30 capturing an image of the tooth T in the narrow image capturing range An and the wide range camera 21 capturing an image of the tooth T in the wide image capturing range Aw. The magnifying glass 1 also includes the three-dimensional position calculator 52 detecting a three-dimensional position of an observation target including at least the tooth T based on the wide range image captured by the wide range camera 21, the blur correction processor 53 correcting a blur of the narrow range image captured by the narrow range camera 30, the correction being made based on the change in a three-dimensional positional relationship between the tooth T, the three-dimensional position of which has been detected by the three-dimensional position calculator 52, and the narrow range camera 30, and the image display portion 40 displaying at least the narrow range image having the blur corrected. Therefore, the tooth T in the narrow image capturing range An may be observed precisely with the blur being suppressed.

This will be described in detail. When the three-dimensional positional relationship between the tooth T and the narrow range camera 30 is changed, a blur is caused to the narrow range image captured by the narrow range camera 30. However, the blur caused to the narrow range image is corrected by the change in the three-dimensional positional relationship between at least the tooth T, the three-dimensional position of which has been calculated based on the wide range image captured by the wide range camera 21, and the narrow range camera 30. Therefore, a clear narrow range image with no blur may be provided. Thus, the tooth T in the narrow image capturing range An may be observed precisely.

The wide range camera 21 may capture an image of the tooth T in the wide image capturing range Aw. Therefore, the wide image capturing range Aw including a site observed by use of the narrow range camera 30 may be observed.

The image display portion 40 displaying at least the narrow range image having the blur corrected is provided. Therefore, the observation may be performed precisely and comprehensively while the narrow range image of a narrow view field and the wide range image of a wide view field are checked together.

Namely, the narrow range image and the wide range image are displayed on the image display portion 40 side by side or in a switching manner. Therefore, while the site in the narrow image capturing range An is observed precisely, the current position of attention in the view field of the wide image capturing range Aw may be checked simultaneously. This improves the operability and the safety.

For example, it is assumed that the observer uses a dental turbine usable to cut the tooth T as the care tool 213 while observing the tooth T with the magnifying glass 1. In this case, if the observer pays attention only to the narrow range observation image display Pn, there is a risk that if the position of the dental turbine is off the narrow image capturing range An, an acute tip bar of the dental turbine that cannot be viewed may inadvertently touch and injure the oral cavity or the skin of the patient. However, the above-described comprehensive observation is now possible. Therefore, even if the position of the dental turbine is off the narrow image capturing range An, the position of the dental turbine may be visually recognized in the wide range observation image display Pw, which displays the wide image capturing range Aw of the tooth T and the vicinity thereof of the patient. This allows the dental turbine to be operated so as not to injure the patient, and thus improves the safety.

As described above, the wide range camera 21, with no additional component, may provide a combined effect of acting as a camera that acquires the three-dimensional position information on the tooth T required for a blur correction and also of acting as a camera for comprehensive observation as described above.

The mechanical vibration that causes the blur is permitted. Therefore, the support arm 300, even in the case of supporting the magnifying glass 1, may have a structure that is low in rigidity, namely, that is compact, lightweight and low-cost.

In the above description, the observation unit Y includes the support arm 300 supporting the magnifying glass 1, and may perform, with no load, an observation with the magnifying glass 1 supported by the support arm 300. The support arm 300 is structured such that the joints 301a are movable to move the magnifying glass 1, supported by the support arm 300, with respect to the tooth T. Therefore, the observation may be performed with the magnifying glass 1 after the support arm 300 is moved to an appropriate position for the tooth T. This allow the observation to be performed in more detail.

The three-dimensional positional relationship between the tooth T, the three-dimensional position of which has been detected by the three-dimensional position calculator 52, and the narrow range camera 30 is calculated based on the three-dimensional position of the tooth T detected based on the wide range image and the known three-dimensional position of the narrow range camera 30 with respect to the wide range camera 21. Alternatively, the image capturing device 20 may be located such that the narrow range camera 30 and the magnifying glass main body 10 are included in the wide range image, and the three-dimensional position and the relative three-dimensional value of each of the tooth T and the narrow range camera 30 may be calculated based on the wide range image including the tooth T, the narrow range camera 30 and the magnifying glass main body 10.

In the above description of the magnifying glass 1, as shown in FIG. 4, the narrow range optical system N and the wide range optical system W are provided separately from each other. The narrow range optical system N and the wide range optical system W may be provided in various forms.

For example, a magnifying glass 1a shown in FIG. 5A may be provided. In the magnifying glass 1a, the wide range optical system W including the wide range camera 21 and the wide range optical path 22, and the narrow range optical system N including the narrow range camera 30 and the narrow range optical path 31, are provided separately from each other. The magnifying glass 1a also includes the common lens 61 transmitting both of an image transmitted through the wide range optical path 22 and an image transmitted through the narrow range optical path 31.

The magnifying glass 1 shown in FIG. 3 includes the wide range image capturing device 20 provided separately from the casing 10a of the magnifying glass main body 10. Unlike the magnifying glass 1, the magnifying glass 1a may have a structure in which the wide range camera 21 and the wide range optical path 22 are provided in the casing 10a in addition to the narrow range camera 30 and the narrow range optical path 31, and the common lens 61 is provided in the objective portion 12.

In FIG. 5A, the common lens 61 is shown as being a single lens. Alternatively, the common lens 61 may be of another form. For example, the common lens 61 may be a lens system including a plurality of lens elements, an optical element such as a mirror, an optical filter, a polarizer, a cover glass or the like, or an optical system having a combination of such elements.

Especially in the case where the optical system acting as the common lens 61 may be equivalently considered as a lens (in the case where a combined focal length may be defined), the direction of the optical axes (arrows from the cameras 21 and 30 toward the tooth T) may be refracted toward the tooth T as shown in FIG. 5A. In this case, the optical axes closer to the cameras 21 and 30 than to the common lens 61 may be made parallel to the casing.

As compared with the case where the optical axes are oblique as shown in FIG. 4, the structure in FIG. 5A provides an effect of, for example, simplifying the design or the assembly process of components that hold the wide range optical system W and the narrow range optical system N to the casing. In addition, the cameras 21 and 30 may be placed on the same plane. In this case, the image sensors included in the cameras 21 and 30 may be mounted on the same electronic board, which may decrease the size and the number of the components and simplify the assembly process.

As shown in FIG. 5B, the magnifying glass 1a may include a wedge plate 61a having a plurality of inclining surfaces, instead of the common lens 61. In this case also, substantially the same effect is provided. The wedge plate 61a is shown as being a single element. Alternatively, for example, a plurality of wedge plates each having a single inclining surface may be combined to form the wedge plate 61a. Needless to say, the common lens 61 or the wedge plate 61a may be replaced with, or combined with, another element having a refraction action such as a mirror, a pentaprism of the like to provide substantially the same effect of refracting the optical axes.

In the magnifying glass 1a having such a structure, an optical image of the tooth T incident on the objective portion 12 is transmitted through the common lens 61, and then is transmitted through the wide range optical path 22 included in the wide range optical system W to be captured by the wide range camera 21 and is also transmitted through the narrow range optical path 31 included in the narrow range optical system N to be captured by the narrow range camera 30. Thus, the optical image of the tooth T may be observed. The magnifying glass 1a provides the above-described effect of the magnifying glass 1 and is advantageous over the magnifying glass 1 as described below. The magnifying glass 1a does not require the casing 20a. In addition, the optical elements such as a lens, a mirror, an optical filter, a polarizer, a cover glass and the like may be made common to the optical systems N and W. As compared with the case where the optical systems N and W each include such optical elements, the magnifying glass 1a may decrease the number of the components and may be more compact.

In the magnifying glass 1a including the common lens 61 or the wedge plate 61a as described above, the common lens 61 or the wedge plate 61a allows the narrow range optical system N and the wide range optical system W to share at least a part of the components. This may simplify the structure and make the magnifying glass main body 10 compact.

The magnifying glass 1b shown in FIG. 6 may be provided. The magnifying glass 1b includes a beam splitter 62 and a common optical path 63, including a lens or the like, provided between the beam splitter 62 and the objective portion 12, instead of the common lens 61 or the wedge plate 61a shown in FIGS. 5A and 5B.

In the magnifying glass 1b having such a structure, an optical image of the tooth T incident on the objective portion 12 is transmitted through the common optical path 63, then is branched by the beam splitter 62 into the narrow range optical system N and the wide range optical system W, and is transmitted through the wide range optical path 22 included in the wide range optical system W to be captured by the wide range camera 21 and is also transmitted through the narrow range optical path 31 included in the narrow range optical system N to be captured by the narrow range camera 30. Thus, the optical image of the tooth T may be observed. The magnifying glass 1b provides the above-described effect of the magnifying glass 1 and may be more compact than the magnifying glass 1.

As shown in FIG. 6A, the beam splitter branches the optical image at 90 degrees into the narrow range optical system N and the wide range optical system W. Therefore, it is not needed to locate the components such as the optical paths, the image sensors and the like in an oblique manner unlike in the magnifying glass 1 shown in FIG. 4. This may simplify the design and the assembly process of the secured components.

In FIG. 6A, the optical image is branched at 90 degrees into the narrow range optical system N and the wide range optical system W. Alternatively, for example, as shown in FIG. 6B, the advancing direction of the optical image may be branched at 90 degrees by the beam splitter 62, and the advancing direction of one of the branched optical images may be further bent at 90 degrees in the opposite direction by a mirror 62a or the like. In this manner, the optical systems N and W in the branched state may be located parallel to each other. In this case, the image sensors included in the cameras 21 and 30 may be mounted on the same electronic board, which may decrease the size, make the assembly process easier, and decrease the number of the components.

In the magnifying glass 1b including the beam splitter 62 and the mirror 62a as described above, the beam splitter 62 and the mirror 62a allow the narrow range optical path 31 and the wide range optical path 22 to share at least a part of the components. This may simplify the structure and make the magnifying glass main body 10 compact.

The magnifying glass 1c shown in FIG. 7A may be provided. In the magnifying glass 1c, the wide range optical system W including the wide range camera 21 and the wide range optical path 22, and the narrow range optical system N including the narrow range camera 30 and the narrow range optical path 31, are provided separately from each other. However, the wide range camera 21 and the narrow range camera 30 are included in one common image sensor 64.

In this case, the common image sensor 64 may be used as being divided into a region acting as the wide range camera 21 and a region acting as the narrow range camera 30. Thus, one common image sensor 64 may have functions of the wide range camera 21 and the narrow range camera 30.

As compared with the magnifying glass 1 shown in FIG. 4 requiring separate electronic boards, the magnifying glass 1c may realize a wide range image and a narrow range image with one electronic board. This may decrease the number of the components, decrease the size, and simplify the assembly process.

In the magnifying glass 1c having such a structure, an optical image of the tooth T incident on the objective portion 12 is transmitted through the wide range optical path 22 included in the wide range optical system W to be captured by the region of the common image sensor 64 that acts as the wide range camera 21 and is also transmitted through the narrow range optical path 31 included in the narrow range optical system N to be captured by the region of the common image sensor 64 that acts as the narrow range camera 30. Thus, the optical image of the tooth T may be observed.

The magnifying glass 1c having such a structure provides the effects of the magnifying glass 1 and the magnifying glass 1a. In addition, since the common image sensor 64 realizes the functions of the narrow range camera 30 and the wide range camera 21, the positional relationship between the narrow range camera 30 and the wide range camera 21 does not change. Therefore, the blur correction on the narrow range image captured by the narrow range camera 30 may be performed accurately with respect to the change in the three-dimensional position of the tooth T based on the wide range image detected by the wide range camera 21. The magnifying glass 1c may also include the common lens 61 or the wedge plate 61a included in the magnifying glass 1a or the beam splitter 62 and the mirror 62a included in the magnifying glass 1b.

Two combinations each including the narrow range optical system N and the wide range optical system W may be respectively provided for the left eye and the right eye. As shown in FIG. 7B, the magnifying glass 1d including two combinations each including the narrow range optical system N and the wide range optical system W may have a structure in which two wide range cameras 21 are respectively provided for the left eye and the right eye, two wide range optical paths 22 are respectively provided for the left eye and the right eye, two narrow range cameras 30 are respectively provided for the left eye and the right eye, and two narrow range optical paths 31 are respectively provided for the left eye and the right eye.

With such a structure, the wide range image capturing devices 20 may act as a three-dimensional camera including two lenses. The narrow range cameras 30 may act as a three-dimensional camera including with two lenses. Therefore, in the magnifying glass 1*d*, the wide range cameras 21 may act as a three-dimensional camera (stereo camera) usable to observe the tooth T three-dimensionally by use of parallax, and the narrow range cameras 30 may act as a three-dimensional camera (stereo camera) usable to observe the tooth T three-dimensionally by use of parallax. This allows the observer to three-dimensionally view both of the image display Pn and the image display Pw displayed on the image display portion 40. Thus, the operability and the degree of satisfaction during the observation may be improved in both of the comprehensive observation and the precise observation.

In the magnifying glass 1*d*, a combination of the narrow range optical system N and the wide range optical system W for the left eye, and a combination of the narrow range optical system N and the wide range optical system W for the right eye, may each include the common lens 61 or the wedge plate 61*a* like in the magnifying glass 1*a* or the beam splitter 62 or the mirror 62*a* and the common optical path 63 like in the magnifying glass 1*b*. With such a structure, the magnifying glass 1*d* may provide substantially the same effect as that of the magnifying glass 1*a* or the magnifying glass 1*b*.

In the magnifying glass 1*d*, the combination of the narrow range camera 30 of the narrow range optical system N and the wide range camera 21 of the wide range optical system W for the left eye, and the combination of the narrow range camera 30 of the narrow range optical system N and the wide range camera 21 of the wide range optical system W for the right eye, may each be included in the common image sensor 64 like in the magnifying glass 1*c*. With such a structure, the magnifying glass 1*d* may provide substantially the same effect as that of the magnifying glass 1*c*.

Like in the magnifying glass 1*d*, two combinations each including the narrow range optical system N and the wide range optical system W may be provided. Alternatively, two narrow range optical systems N and one wide range optical system W, or one narrow range optical system N and two wide range optical systems W, may be provided.

As shown in FIG. 8A, the magnifying glass 1 may include the projector 70 irradiating at least the tooth T. Specifically, the projector 70 projects projection light L toward the tooth T. In this example, an irradiation range of the projection light L is set such that the projection light L irradiates a range corresponding to the narrow range image capturing region. For example, as shown in FIG. 8A, the projector 70 is located such that the optical axis of the camera and the optical axis of the projection light cross each other at an optimal focal point of the narrow range camera.

The projection light L may be kept on while the magnifying glass 1 is used, or may be blinked at a predetermined timing.

The projection light L may be, for example, pattern projection light La having a lattice pattern or the like. With such an arrangement, for example, the wide range camera may be a three-dimensional camera capable of calculating a three-dimensional surface shape (e.g., three-dimensional camera based on pattern projection-type trigonometry). Thus, the precision with which the three-dimensional calculator 52 calculates the three-dimensional position of the characteristic point on the surface shape, and the precision with which the omnifocal narrow range image described below is generated, are improved.

The irradiation range of each of projection light L and projection light La is not limited to the narrow image capturing range An, and may be the wide image capturing range Aw including the narrow image capturing range An. In this case, it is advantageous that that the narrow image capturing range An and the wide image capturing range Aw in the irradiation range have different irradiation states, for example, different levels of brightness, different colors, and different patterns of the pattern projection light La.

In the case where, for example, the wide range camera 21 and the narrow range camera 30 are different from each other in the image capturing range or the parameter defining the exposure sensitivity such as the F-number, the shutter speed or the like, it is advantageous to set the amount of light and the color in accordance with the camera. It is also advantageous that the narrow image capturing range An and the wide image capturing range Aw have different patterns of the pattern projection light La in accordance with an algorithm usable to calculate a three-dimensional surface shape by the wide range camera 21 or an algorithm usable to generate an omnifocal narrow range image described below.

In the case where the projector 70 is provided as described above, the narrow range camera 30 may capture a bright narrow range image, and the narrow image capturing range An corresponding to the narrow range image to be captured by the narrow range camera 30 may be displayed brightly. Therefore, the narrow image capturing range An may be clearly depicted in the wide range image captured by the wide range camera 21.

In the case where the wide image capturing range Aw including the narrow image capturing range An is to be irradiated, as well as in the case where the narrow image capturing range An is to be irradiated, the narrow image capturing range An and the wide image capturing range Aw may have different irradiation states, for example, different levels of brightness, different colors or different patterns. In this manner, the above-described clear depiction function may be realized.

The projector 70 may be included in each of the magnifying glasses 1*a*, 1*b* and 1*c*. In the case of being included in the magnifying glass 1*d*, one projector 70 may be provided for the narrow range optical system N and the wide range optical system W for the left eye while another one projector 70 may be provided for the narrow range optical system N and the wide range optical system W for the right eye, or one projector 70 may be provided for two narrow range optical systems N and two wide range optical systems W. In the case where one projector 70 is provided for the narrow range optical system N and the wide range optical system W for the left eye while another one projector 70 is provided for the narrow range optical system N and the wide range optical system W for the right eye, the projector 70 for the left eye and the projector 70 for the right eye may be different from each other in the wavelength (color) of the projection light L, the polarization state and the blinking timing.

As described above, the projector 70 projects the projection light L or La toward at least the tooth T to be captured by the narrow range camera 30 during continuous image capturing performed under the control of the controller 50. The projector 70 projects the projection light L or La toward the tooth T observed by use of the narrow range camera 30 of a narrow view field. Therefore, as shown in FIG. 9B, the tooth T observed by use of the narrow range camera 30 may be clearly depicted in the wide range image captured by the wide range camera 21.

Namely, as shown in a wide range observation image display Pw' shown in FIG. 9B, the projection light L or La thus projected may clearly depict a site Pe, in the wide range image, that is captured as the narrow range image. The wide range image and the narrow range image may be displayed on the image display portion 40 side by side. In this case, the observation site in the entirety is made clear, and thus the operability may be improved.

The pattern projection light La projected by the projector 70 is projected toward at least the tooth T, the image of which is captured by the narrow range camera 30. Therefore, for example, even if being a homogenous structural body with no decorative pattern, the tooth T may be provided with a pattern, so that in the process of generating the omnifocal narrow range image described below, the contrast may be detected easily. Thus, a narrow range image that is clearer and has a greater depth of field may be generated with high precision.

As shown in FIG. 8B, the magnifying glass 1e may be provided. The magnifying glass 1e includes the projectors 70 (70a and 70b) respectively in the narrow range optical system N and the wide range optical system W. In this case, the magnifying glass 1e may include beam splitters 71 respectively in the optical paths 31 and 22 in addition to the projectors 70 (70a and 70b) provided in the narrow range optical system N and the wide range optical system W.

The magnifying glass 1e having such a structure provides the above-described effect of the magnifying glass 1. In addition, in the magnifying glass 1e, the projection light L or La projected from the projector 70 passes the beam splitters 71 to be projected toward the tooth T, and the light reflected by the tooth T passes the beam splitters 71 to be captured by the narrow range camera 30 and the wide range camera 21. Thus, the projection light L or La may be observed.

The projectors 70 (70a and 70b) are provided separately from each other. Therefore, as compared with the case where there is one projector 70, the degree of freedom of design of the projectors 70 is improved in the case where the image capturing ranges Aw and An have different irradiation states as described above.

In the case where the projector 70a of the narrow range optical system N and the projector 70b of the wide range optical system W project the projection light L or La at the same time, the projectors 70a and 70b may be different from each other in the wavelength (color) of the projection light L or La, the polarization state, the blinking timing, the decorative pattern or the like.

The omnifocal magnifying glass 1f shown in FIG. 12 may be provided as another example of the magnifying glass 1. The omnifocal magnifying glass 1f includes the components of the magnifying glass 1e shown in FIG. 8B and also a focal point variable lens 72 in the narrow range optical path 31 of the narrow range optical system N in addition of the beam splitter 71. As shown in FIG. 1B, the magnifying glass 1f further includes a focal point adjuster 73 adjusting the position of the focal point variable lens 72 with respect to the narrow range camera 30 in the narrow range optical system N, and also includes, in the controller 50, a focal point adjustment controller 54 controlling the focal point adjuster 73 and a projection controller 55 controlling the projection of the pattern projection light La by the projector 70.

The narrow range optical system N of the omnifocal magnifying glass 1f having such a structure acts as follows in the case where, for example, the focal point variable lens 72 is of a type that mechanically moves the position of the lens. As shown in FIG. 13, the position of the focal point variable lens 72 with respect to the narrow range camera 30 is adjusted by the focal point adjuster 73. As a result, the position of the focal point of the narrow range camera 30 (i.e., the position in the height direction of the plane shown as the narrow image capturing range An in FIG. 13) may be swept over a predetermined range R in the direction of the optical axis. Thus, the narrow range image may be captured while the focal point is swept.

As shown in FIG. 14, the focal point adjuster 73 is controlled to adjust the focal point variable lens 72. Thus, while the position of the focal point is sequentially swept in the height direction from a top portion of the tooth T, the narrow range image may be captured by the narrow range camera 30 at a timing where the focal point arrives at a predetermined position. In this manner, a plurality of narrow range images at different focal points may be provided. The plurality of narrow range images at the different focal points are synthesized by the image generator 51. As a result, an omnifocal narrow range image that is focused over the entire region in the height direction, which is the direction of the optical axis of the narrow range camera 30, namely, an omnifocal narrow range image that has an expanded depth of field, may be provided. In FIG. 14, the position of the focal point is sequentially swept in the height direction from the top portion of the tooth T. Alternatively, the position of the focal point may be swept in an opposite direction, or may be swept repeatedly periodically.

Specifically, an omnifocal narrow range image, namely, a narrow range image having an expanded depth of field, may be generated by synthesizing the plurality of narrow range images as follows.

(1) First, images of the tooth T are continuously captured by the narrow range camera 30 while the position of the focal point is swept on the tooth T by a method of, for example, mechanically driving a lens or the like in the narrow range optical path 31 of the narrow range camera 30.

(2) The amount of contrast is calculated (quantization of whether the narrow range image is blurred or focused is performed) for each of pixels included in each of the narrow range images. While the position of the focal point is swept by, for example, one reciprocal movement (or half reciprocal movement) of the lens, the pixel value at the time when the amount of contrast exhibits the maximum value is used for the narrow range image to be displayed on the image display portion 40.

The amount of contrast may be calculated by a known method of using the Laplacian operator, a differential filter or the like.

If the narrow range image is blurred, the amount of contrast may, for example, exhibit the maximum value a plurality of times in the calculation of (2). In this case, the narrow range image displayed on the image display portion 40 may be distorted or may have noise. According to one or more embodiments of the present invention, the calculation is performed based on the narrow range image having the blur corrected. Therefore, the above-described situation of the noise or the like may be resolved, and the operability for the observer may be improved.

The above-described calculation procedure may be performed at high speed by use of a hardware processor such as an FPGA or the like.

The focal point of the narrow range camera 30 may be moved by the above-described method of securing the narrow range camera 30 and mechanically moving the position of the focal point of the lens or the like included in the narrow range optical path 31, or by a method of electrically controlling the focal point variable lens such as a liquid lens or the like to adjust the focal point. Alternatively, the narrow range camera 30 may be physically moved while the focal length thereof is kept at a predetermined distance, to move the position of the focal point. Still alternatively, the entirety of the magnifying glass main body 10 may be moved.

In the case where the position of the focal point is swept repeatedly in the above-described structure including the mechanical movable portion, it is advantageous to use a counterweight (weight that moves in a direction opposite to the movable portion) to counteract the vibration that occurs in accompaniment with the movement of the center of gravity. The use of the counterweight may suppress an unnecessary vibration and allows the omnifocal magnifying glass if to operate at low noise. Thus, the observation may be performed more precisely.

As described above, the omnifocal magnifying glass if includes the focal point adjustment controller 54 controlling the continuous image capturing performed while the position of the focal point of the narrow range camera 30 is moved with respect to the tooth T, and also includes the image generator 51 synthesizing a plurality of narrow range images captured by the continuous image capturing to generate an omnifocal narrow range image, namely, a narrow range image having a great depth of field. Therefore, the observation may be performed more precisely based on the narrow range image having a great depth of field.

This will be described in detail. The narrow range camera 30 captures an image of the narrow image capturing range An of the tooth T at high magnification. However, the narrow range image captured by the narrow range camera 30 has a small depth of field, namely, has a narrow range that is focused in the depth direction. Therefore, the range that may be observed precisely tends to be narrow. Nonetheless, the continuous image capturing is performed while the position of the focal point of the narrow range camera 30 is moved, and the plurality of narrow range images captured as a result of the continuous image capturing are synthesized to generate a narrow range image having a great depth of field. Namely, the narrow image capturing range An, of the tooth T, captured at high magnification and including a wide region focused in the depth direction is generated. Therefore, the observation may be performed precisely.

The plurality of narrow range images captured as a result of the continuous image capturing performed while the position of the focal point is moved have the blur corrected. Therefore, the narrow range images captured as a result of the continuous image capturing may be synthesized with high precision to generate, at high precision, a narrow range image that is clear and has a great depth of field.

Namely, the wide range camera 21 may provide a combined effect of acting to correct the blur, being also usable to improve the precision of the generation, by the narrow range camera 30, of an image having a great depth of field described above, and performing the three-dimensional measurement on the tooth T precisely based on the comprehensive observation, the processing of the clear depiction portion and the focal point position information described below by use of the same wide range camera 21 with no increase in the number of components.

As represented by the dashed line in FIG. 1B, the omnifocal magnifying glass 1f may include a three-dimensional shape meter 56 measuring a three-dimensional shape of at least the tooth T captured by the narrow range camera 30 based on the focal point position information on the position of the focal point moving during the continuous image capturing performed under the control of the controller 50.

The provision of the three-dimensional shape meter 56 may realize the capturing of a clear narrow range image of the narrow image capturing range An having a great depth of field and also provide a three-dimensional shape of the tooth T.

Specifically, in the above-described process of (2) of generating the omnifocal narrow range image, the amount of contrast exhibiting the maximum value at a certain pixel is equivalent to the moving position of the focal point matching the position of the surface of the tooth T, which is the observation site.

The focal point position information on the moving position of the focal point may be associated with a control state of a narrow range image capturing portion controller (information on the voltage input to the liquid lens, information on the voltage input to an actuator or the like that moves the lens, or information on the current position of the lens mechanically moving, the position being measurable by use of an encoder sensor or the like). The association is made possible by a calibration process of, for example, capturing, in advance, an image of a reference object, the shape of which is known. The three-dimensional shape of the observation site may be provided based on the process of generating the above-described narrow range image having a great depth of field and the above-described focal point position information.

If the plurality of images captured continuously in order to generate the narrow range image having a great depth of field are blurred, the amount of contrast may, for example, exhibit the maximum value a plurality of times in the process of (2). In this case, the measured three-dimensional shape may be distorted or may have noise. According to one or more embodiments of the present invention, the process of measuring the three-dimensional shape is performed based on the narrow range image having the blur corrected. Therefore, the above-described situation of the noise or the like may be resolved, and the three-dimensional shape may be measured more precisely.

In order to detect the three-dimensional position of the tooth T or the wide image capturing rang Aw from the wide range image captured by the wide range camera 21, a plurality of characteristic points may be provided in the oral cavity. With such an arrangement, the three-dimensional position may be calculated more accurately. An example thereof is shown in FIG. 11. The patient, who is the observation target, bites occlusion paper, and as a result, dots (color points Pc) of red, blue or the like are transferred to the teeth of the patient. The transferred color points Pc may be used as the characteristic points. The movement of these color points Pc is tracked by the wide range camera 21, and thus the three-dimensional position and the movement of the dental arch of the patient may be recognized. Therefore, the blur correction on the narrow range image captured by the narrow range camera 30 may be performed more accurately for the change in the three-dimensional position of the tooth T based on the wide range image detected by the wide range camera 21.

In order to prevent the characteristic points from being made difficult to be viewed as a result of the transferred color points being concealed behind the inside of the cheek, it is advantageous to use an opener that exposes the hard tissue (i.e., the dental arch of the patient). Herein, the "occlusion paper" is not limited to the paper widely available commercially under the name of the "occlusion paper", namely, a sheet-like thin film to which a red or blue pigment may be transferred. The "occlusion paper" encompasses any item which, when being bitten with the teeth, transfers a color or an optical feature to a position corresponding to the occlusion (paint such as biosafe pigment, pressure-sensitive adhesive, pressure-sensitive adhesive sheet, microcapsule, particle, substance that emits fluorescent light upon being irradiated with the projection light L, etc.). The "occlusion paper" encompasses any item of a sheet shape, a thick shape, an impressive tray shape, and a mouthpiece shape (sprint shape) that may be inserted into the mouth.

As described above, the tooth T is the desired position in the oral cavity, and the three-dimensional position calculator 52 detects, in the wide range image, a plurality of colored sites colored by the occlusion paper on the surface of the tooth in the oral cavity. In this manner, the three-dimensional position may be detected with high precision with no need to, for example, provide a separate component acting as a characteristic point such as a ball marker or the like.

The controller 50 of the observation unit Y including the magnifying glass 1 (1a through 1f) having such a structure may be connected with a monitor 240. In this case, the images captured by the narrow range camera 30 and the wide range camera 21 may be displayed on the monitor 240, as well as on the image display portion 40, to be observed. In, for example, FIG. 2, the monitor 240 is shown as being set on the treatment stand pole 230. Alternatively, the monitor 240 may be set at a different position, for example, on the support arm 300, a support arm different from the support arm 300, the wall, the ceiling or the like.

Although not shown, the controller 50 of the observation unit Y may be connected with an external monitor other than the monitor 240. Alternatively, the controller 50 may be connected by, for example, a wireless communication device, with a head-mounted display (HMD), an eyeglass-type head-up display (HUD), or any other display device of a head gear type, a helmet type, a sun visor type, a band type, an eyeglass type or a type attachable by a clip to the frame of general eyeglasses normally used by the observer for correcting the eyesight or the like.

As described above, the monitor 240 or a plurality of display devices may be provided. In this manner, even in the case where the observer moves to any of various positions or in the case where there are a plurality of observers, the narrow range image having the blur corrected may be displayed from various viewing positions by the monitor 240 different from the image display portion 40. Thus, the narrow range image having the blur corrected may be observed. In, for example, dental care, the monitor 240 may be set at a position viewable from the patient, who is an observation subject. This is effective to explain the situation of the care to the patient or to obtain informed consent.

The image display portion 40 may not be located in the magnifying glass 1 (1a through 1f), and the image display portion 40 of the magnifying glass 1 (1a through 1f) may be located on an HMD, an HUD, or any other display device of a head gear type, a helmet type, a sun visor type, a band type, an eyeglass type or a type attachable by a clip to the frame of general eyeglasses normally used by the observer for correcting the eyesight or the like. In this case, the image display portion 40 is separated from the main body of the magnifying glass 1, and as a result, a head-mountable magnifying glass is provided.

The HMD or the HUD usable to attach the image display portion 40 to the head of the observer may display, for observation, the narrow range image having the blur corrected with no restriction on the movement of the head.

The tooth T according to one or more embodiments of the present invention corresponds to the observation site in the above-described embodiment; and similarly, the image capturing portion corresponds to the cameras 30 or 21;

the observation device corresponds to the magnifying glass 1;

the narrow range corresponds to the narrow image capturing range An;

the narrow range image capturing portion corresponds to the narrow range camera 30;

the wide range corresponds to the wide image capturing range Aw;

the wide range image capturing portion corresponds to the wide range camera 21;

the wide range image corresponds to the wide range image;

the three-dimensional position detector corresponds to the three-dimensional position calculator 52;

the narrow range image corresponds to the narrow range image;

the blur corrector corresponds to the blur correction processor 53;

the image display portion corresponds to the image display portion 40;

the optical route of the narrow range image capturing portion corresponds to the narrow range optical path 31;

the optical route of the wide range image capturing portion corresponds to the wide range optical path 22;

the narrow range image capturing controller corresponds to the controller 50;

the narrow range image generator corresponds to the image generator 51;

the light corresponds to the projection light L or La;

the light projector corresponds to the projector 70;

the three-dimensional shape meter corresponds to the three-dimensional shape meter 56;

the head-mountable display device corresponds to the HMD or the HUM;

the support corresponds to the support arm 300;

the observation unit corresponds to the observation unit Y; and the display device corresponds to the monitor 240 or the external monitor. However, one or more embodiments of the present invention are not limited to the above-described embodiment.

For example, in the above, the observation target of the magnifying glass 1, the observation unit Y and the care unit X is the tooth T of the patient, and the observation in the dental care is described. The observation target is not limited to the tooth, and may be a site inside the tooth or a site in the oral cavity such as the gum or the like. The magnifying glass 1, the observation unit Y and the care unit X are not limited to being used in the care, and may be used in the training or the like. The magnifying glass 1, the observation unit Y and the care unit X are not limited to being used in the dental care, and may be used in other fields in which precise care is needed, for example, otorhinolaryngology, brain surgery and the like. The magnifying glass 1 and the observation unit Y are not limited to being used in the dental or medical field, and may be used in the fields in which precision is required, for example, biology and the like.

The three-dimensional position calculator 52 compares a wide range image currently captured and at least one wide range image captured at a timing before the current timing, among wide range images captured continuously. Then, the three-dimensional position calculator 52 finds what type of motion is made by a characteristic site (characteristic point) in the images by use of a technique such as template matching, characteristic point matching or the like to detect the three-dimensional position. The characteristic point may be in any other form as long as being rigidly secured to the tooth T to be observed with no blur. It is effective to select and track a characteristic point of a form suitable to the wavelength of the light that may be captured by the camera 21 or suitable to the tracking algorithm (e.g., a retroreflective ball marker exhibiting strong reflection for infrared light).

It is more preferred that a removal process is performed to remove items other than the tracking target in the image (to remove, for example, the hand of the observer that moves regardless of the tooth of the observation subject, the surgery tools, and the soft tissue of the observation subject other than the oral cavity). An example of the removal process may be to specify a site other than tooth by use of the color difference. Alternatively, a marker having a particular shape or particular optical reflection and emission characteristics may be provided and secured to the tooth of the observation subject rigidly. In this manner, the marker may be used as the characteristic point.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims

REFERENCE SIGNS LIST

1 Magnifying glass
21 Wide range camera
22 Wide range optical path
30 Narrow range camera
31 Narrow range optical path
40 Image display portion
50 Controller
51 Image generator
52 Three-dimensional position calculator
53 Blur correction processor
56 Three-dimensional shape meter
70, 70a Irradiation portion
240 Monitor
300 Narrow range camera
An Narrow image capturing range
Aw Wide image capturing range
L Projection light
La Pattern projection light
T Tooth
Y Observation unit

The invention claimed is:

1. An observation device capturing an image of an image capturing site for observation, the observation device comprising:
an image capturing portion capturing the image of the image capturing site, the image capturing portion including a narrow range image capturing portion capturing an image of the observation site in a narrow range and a wide range image capturing portion capturing an image of the observation site in a wide range;
a three-dimensional position detector detecting a three-dimensional position of at least the observation site based on a wide range image captured by the wide range image capturing portion;
a blur corrector correcting a blur of a narrow range image captured by the narrow range image capturing portion, based on a change in a three-dimensional positional relationship between the observation site, the three-dimensional position of which has been detected by the three-dimensional position detector, and the narrow range image capturing portion;
an image display portion displaying at least the narrow range image having the blur corrected, among the narrow range image having the blur corrected and the wide range image;
an imaging part including a narrow range imaging part and a wide range imaging part, wherein the narrow imaging part comprises a first optical path to observe the observation site and the wide imaging part comprises a second optical path to observe the observation site;
a narrow range image capturing portion controller controlling continuous image capturing performed while a focal point position of the narrow range image capturing portion is moved with respect to the observation site; and
a narrow range image generator synthesizing a plurality of narrow range images captured as a result of the continuous image capturing to generate the narrow range image having a great depth of field,
wherein the focal point position of the narrow range image capturing portion is swept by at least one of one reciprocal movement and a half reciprocal movement of a lens of the narrow image capturing portion over a predetermined distance,
wherein the observation site being a desired site in an oral cavity, and the three-dimensional position detector detecting the three-dimensional position of the observation site by detecting, in the wide range image, a plurality of colored sites, colored by occlusion paper, on a surface of a tooth in the oral cavity,
wherein at least the image display portion being of a head-mountable type mountable on the head of an observer, and
wherein a pixel value at the time when an amount of contrast exhibits the maximum value, which is equivalent to a moving position of the focal point position of the narrow range image capturing portion matching a position of the surface of the tooth, is used for the narrow range image to be displayed on the image display portion.

2. The observation device according to claim 1, the narrow range image capturing portion and the wide range image capturing portion sharing at least a part of optical routes thereof.

3. The observation device according to claim 1, further comprising a light projector projecting light toward at least the observation site, the image of which is to be captured by the narrow range image capturing portion, at the time of performing the continuous image capturing under the control of the narrow range image capturing portion controller.

4. The observation device according to claim 1, further comprising a three-dimensional shape meter measuring a three-dimensional shape of at least the observation site, the image of which is to be captured by the narrow range image capturing portion, the measurement being performed based on focal point position information on the focal point position that is moving during the continuous image capturing performed under the control of the narrow range image capturing portion controller.

5. An observation unit, comprising: the observation device according to claim 1; and a support supporting at least the narrow range image capturing portion of the observation device.

6. The observation unit according to claim 5, the support allowing at least the narrow range image capturing portion, supported by the support, of the observation device to move with respect to the observation site.

7. The observation unit according to claim 5, further comprising a display device displaying at least the narrow range image having the blur corrected.

8. The observation unit according to claim 7, the display device being of a head-mountable type mountable on the head of an observer.

9. An observation method for capturing an image of an observation site, for observation, by an image capturing portion of an observation device, the observation method comprising:
- detecting a three-dimensional position of at least the observation site based on a wide range image captured by a wide range image capturing portion included in the image capturing portion;
- correcting a blur of a narrow range image captured by a narrow range image capturing portion included in the image capturing portion, based on a three-dimensional positional relationship between the observation site, the three-dimensional position of which has been detected, and the narrow range image capturing portion;
- displaying at least the narrow range image having the blur corrected, among the narrow range image having the blur corrected and the wide range image;
- observing the observation part via an imaging part including a narrow range imaging part and a wide range imaging part, wherein the narrow imaging part comprises a first optical path to observe the observation site and the wide imaging part comprises a second optical path to observe the observation site;
- performing continuous image capturing while moving, with respect to the observation site, a focal point position of the narrow range image capturing portion; and
- synthesizing a plurality of narrow range images captured as a result of the continuous image capturing to generate a narrow range image having a great depth of field,
- wherein the focal point position of the narrow range image capturing portion is swept by at least one of one reciprocal movement and a half reciprocal movement of a lens of the narrow image capturing portion over a predetermined distance,
- wherein the observation site being a desired site in an oral cavity, and the three-dimensional position of the observation site is detected by, in the wide range image, a plurality of colored sites, colored by occlusion paper, on a surface of a tooth in the oral cavity,
- wherein the narrow range image having the blur corrected is displayed on an image display portion, which is a head-mountable type mountable on the head of an observer, and
- wherein a pixel value at the time when an amount of contrast exhibits the maximum value, which is equivalent a moving position of the focal point position of the narrow range image capturing portion matching the surface of the tooth, is used for the narrow range image to be displayed on the image display portion.

* * * * *